(12) United States Patent
Vargas et al.

(10) Patent No.: US 6,471,713 B1
(45) Date of Patent: *Oct. 29, 2002

(54) SYSTEM FOR DEPLOYING AN ANASTOMOSIS DEVICE AND METHOD OF PERFORMING ANASTOMOSIS

(75) Inventors: Jaime Vargas, Palo Alto; Stephen A. Yencho, Menlo Park; Jamey Nielsen, San Francisco; Michael Hendricksen, Redwood City; Bernard A. Hausen, Menlo Park; Russell C. Mead, Jr., Mountain View; Heather Klaubert, Redwood City; Brendan M. Donohoe; Theodore Bender, both of San Francisco, all of CA (US)

(73) Assignee: Cardica, Inc., Menlo Park, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/709,373

(22) Filed: Nov. 13, 2000

(51) Int. Cl.⁷ ............................................. A61B 17/04
(52) U.S. Cl. ..................................................... 606/153
(58) Field of Search ........................................ 606/153

(56) References Cited

U.S. PATENT DOCUMENTS

| | | |
|---|---|---|
| 2,370,776 A | 3/1945 | Carlson |
| 3,254,650 A | 6/1966 | Collito |
| 3,254,651 A | 6/1966 | Collito |
| 3,519,187 A | 7/1970 | Kapitanov et al. |
| 3,774,615 A | 11/1973 | Lim et al. |
| 4,118,806 A | 10/1978 | Porier et al. |
| 4,214,587 A | 7/1980 | Sakura, Jr. |
| 4,217,664 A | 8/1980 | Faso |
| 4,350,160 A | 9/1982 | Kolesov et al. |
| 4,352,358 A | 10/1982 | Angelchik |
| 4,366,819 A | 1/1983 | Kaster |
| 4,368,736 A | 1/1983 | Kaster |
| 4,503,568 A | 3/1985 | Madras |
| 4,523,592 A | 6/1985 | Daniel |
| 4,534,761 A | 8/1985 | Raible |
| 4,553,542 A | 11/1985 | Schenck et al. |
| 4,577,631 A | 3/1986 | Kreamer |
| 4,589,416 A | 5/1986 | Green |
| 4,593,693 A | 6/1986 | Schenck |
| 4,603,693 A | 8/1986 | Conta et al. |
| 4,607,637 A | 8/1986 | Berggren et al. |
| 4,624,255 A | 11/1986 | Schenck et al. |
| 4,624,257 A | 11/1986 | Berggren et al. |
| 4,657,019 A | 4/1987 | Walsh et al. |
| 4,665,906 A | 5/1987 | Jervis |

(List continued on next page.)

FOREIGN PATENT DOCUMENTS

| | | |
|---|---|---|
| DE | 29713335.7 | 11/1997 |
| DE | 19732234 | 1/1999 |
| EP | 0517252 | 12/1992 |

(List continued on next page.)

Primary Examiner—Gary Jackson
(74) Attorney, Agent, or Firm—Brian A. Schar; Cindy A. Lynch

(57) ABSTRACT

A deployment system for forming an incision in a target vessel, for placement of an anastomosis device and for deployment of an anastomosis device having an inner flange formed by radial expansion of the device and an outer flange formed by axial compression of the device.

18 Claims, 19 Drawing Sheets

U.S. PATENT DOCUMENTS

| | | |
|---|---|---|
| 4,721,109 A | 1/1988 | Healey |
| 4,747,407 A | 5/1988 | Liu et al. |
| 4,752,024 A | 6/1988 | Green et al. |
| 4,773,420 A | 9/1988 | Green ..................... 227/178.1 |
| 4,861,330 A | 8/1989 | Voss |
| 4,875,815 A | 10/1989 | Phillips, II |
| 4,883,453 A | 11/1989 | Berry et al. |
| 4,892,098 A | 1/1990 | Sauer |
| 4,907,591 A | 3/1990 | Vasconcellos et al. |
| 4,917,087 A | 4/1990 | Walsh et al. |
| 4,917,090 A | 4/1990 | Berggren et al. |
| 4,917,091 A | 4/1990 | Berggren et al. |
| 4,930,674 A | 6/1990 | Barak |
| 5,005,749 A | 4/1991 | Aranyi |
| 5,015,238 A | 5/1991 | Solomon et al. |
| 5,062,842 A | 11/1991 | Tiffany |
| 5,089,006 A | 2/1992 | Stiles |
| 5,104,025 A | 4/1992 | Main et al. |
| 5,119,983 A | 6/1992 | Green et al. |
| 5,129,913 A | 7/1992 | Ruppert |
| 5,156,613 A | 10/1992 | Sawyer |
| 5,156,619 A | 10/1992 | Ehrenfeld |
| 5,171,262 A | 12/1992 | MacGregor |
| 5,178,634 A | 1/1993 | Ramos Martinez |
| 5,187,796 A | 2/1993 | Wang et al. |
| 5,192,289 A | 3/1993 | Jessen |
| 5,193,731 A | 3/1993 | Aranyi |
| 5,205,459 A | 4/1993 | Brinkerhoff et al. |
| 5,211,683 A | 5/1993 | Maginot |
| 5,217,474 A | 6/1993 | Zacca et al. |
| 5,221,281 A | 6/1993 | Klicek |
| 5,222,963 A | 6/1993 | Brinkerhoff et al. |
| 5,234,447 A | 8/1993 | Kaster et al. |
| 5,250,058 A | 10/1993 | Miller et al. |
| 5,250,060 A | 10/1993 | Carbo et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,290,298 A | 3/1994 | Rebuffat et al. |
| 5,292,053 A | 3/1994 | Bilotti et al. |
| 5,304,220 A | 4/1994 | Maginot |
| 5,314,435 A | 5/1994 | Green et al. |
| 5,314,468 A | 5/1994 | Ramos Martinez |
| 5,326,205 A | 7/1994 | Anspach, Jr. et al. |
| 5,333,773 A | 8/1994 | Main et al. |
| 5,336,233 A | 8/1994 | Chen |
| 5,350,104 A | 9/1994 | Main et al. |
| 5,354,302 A | 10/1994 | Ko |
| 5,364,389 A | 11/1994 | Anderson |
| 5,366,462 A | 11/1994 | Kaster et al. |
| 5,392,979 A | 2/1995 | Green et al. |
| 5,395,030 A | 3/1995 | Kuramoto et al. |
| 5,395,311 A | 3/1995 | Andrews |
| 5,401,131 A | 3/1995 | Yoshino |
| 5,443,497 A | 8/1995 | Venbrux |
| 5,447,514 A | 9/1995 | Gerry et al. |
| 5,454,825 A | 10/1995 | Van Leeuwen |
| 5,456,712 A | 10/1995 | Maginot |
| 5,456,714 A | 10/1995 | Owen |
| 5,464,449 A | 11/1995 | Ryan et al. |
| 5,465,895 A | 11/1995 | Knodel et al. |
| 5,478,354 A | 12/1995 | Tovey et al. |
| 5,503,635 A | 4/1996 | Sauer et al. |
| 5,515,478 A | 5/1996 | Wang |
| 5,522,834 A | 6/1996 | Fonger et al. |
| 5,524,180 A | 6/1996 | Wang et al. |
| 5,533,661 A | 7/1996 | Main et al. |
| 5,540,677 A | 7/1996 | Sinofsky |
| 5,553,198 A | 9/1996 | Wang et al. |
| 5,556,405 A | 9/1996 | Lary |
| 5,558,667 A | 9/1996 | Yarborough et al. |
| 5,571,167 A | 11/1996 | Maginot |
| 5,643,340 A | 7/1997 | Nunokawa |
| 5,645,520 A | 7/1997 | Nakamura et al. |
| 5,657,429 A | 8/1997 | Wang et al. |
| 5,669,918 A | 9/1997 | Balazs et al. |
| 5,669,934 A | 9/1997 | Sawyer |
| 5,676,670 A | 10/1997 | Kim |
| 5,693,088 A | 12/1997 | Lazarus |
| 5,695,504 A | 12/1997 | Gifford, III et al. |
| 5,702,412 A | 12/1997 | Popov et al. |
| 5,707,362 A | 1/1998 | Yoon |
| 5,707,380 A | 1/1998 | Hinchliffe et al. |
| 5,709,335 A | 1/1998 | Heck |
| 5,709,693 A | 1/1998 | Taylor |
| 5,725,544 A | 3/1998 | Rygaard |
| 5,725,553 A | 3/1998 | Moenning |
| 5,732,872 A | 3/1998 | Bolduc et al. |
| 5,754,741 A | 5/1998 | Wang et al. |
| 5,755,778 A | 5/1998 | Kleshinski |
| 5,762,458 A | 6/1998 | Wang et al. |
| 5,779,718 A | 7/1998 | Green et al. |
| 5,792,135 A | 8/1998 | Madhani et al. |
| 5,797,900 A | 8/1998 | Madhani et al. |
| 5,797,920 A | 8/1998 | Kim |
| 5,799,661 A | 9/1998 | Boyd et al. |
| 5,799,857 A | 9/1998 | Robertson et al. |
| 5,807,377 A | 9/1998 | Madhani et al. |
| 5,814,073 A | 9/1998 | Bonutti |
| 5,815,640 A | 9/1998 | Wang et al. |
| 5,817,113 A | 10/1998 | Gifford, III et al. |
| 5,827,316 A | 10/1998 | Young et al. |
| 5,833,698 A | 11/1998 | Hinchliffe et al. |
| 5,841,950 A | 11/1998 | Wang et al. |
| 5,855,583 A | 1/1999 | Wang et al. |
| 5,868,763 A | 2/1999 | Spence et al. |
| 5,875,782 A | 3/1999 | Ferrari et al. |
| 5,878,193 A | 3/1999 | Wang et al. |
| 5,879,371 A | 3/1999 | Gardiner et al. |
| 5,881,943 A | 3/1999 | Heck et al. |
| 5,893,369 A | 4/1999 | LeMole |
| 5,904,697 A | 5/1999 | Gifford, III et al. |
| 5,907,664 A | 5/1999 | Wang et al. |
| 5,911,036 A | 6/1999 | Wright et al. |
| 5,915,616 A | 6/1999 | Viola et al. |
| 5,921,995 A | 7/1999 | Kleshinski |
| 5,944,730 A | 8/1999 | Nobles et al. |
| 5,947,363 A | 9/1999 | Bolduc et al. |
| 5,957,363 A | 9/1999 | Heck |
| 5,968,089 A | 10/1999 | Krajicek |
| 5,976,159 A | 11/1999 | Bolduc et al. |
| 6,001,124 A | 12/1999 | Bachinski |
| 6,007,544 A | 12/1999 | Kim |
| 6,013,190 A | 1/2000 | Berg et al. |
| 6,015,416 A | 1/2000 | Stefanchik et al. |
| 6,022,367 A | 2/2000 | Sherts |
| 6,024,748 A | 2/2000 | Manzo et al. |
| 6,030,370 A | 2/2000 | Kupka et al. |
| 6,030,395 A | 2/2000 | Nash et al. |
| 6,036,699 A | 3/2000 | Andreas et al. |
| 6,036,700 A | 3/2000 | Stefanchik et al. |
| 6,036,702 A | 3/2000 | Bachinkski et al. |
| 6,036,703 A | 3/2000 | Evans et al. |
| 6,036,704 A | 3/2000 | Yoon |
| 6,036,705 A | 3/2000 | Nash et al. |
| 6,050,472 A | 4/2000 | Shibata |
| 6,053,390 A | 4/2000 | Green et al. |
| 6,056,762 A | 5/2000 | Nash et al. |
| 6,066,144 A | 5/2000 | Wolf et al. |
| 6,066,148 A | 5/2000 | Rygaard |
| 6,068,637 A | 5/2000 | Popov et al. |

| | | | | | |
|---|---|---|---|---|---|
| 6,074,416 | A | 6/2000 | Berg et al. | WO | 98/42262 10/1998 |
| 6,080,167 | A | 6/2000 | Lyell | WO | 98/47430 10/1998 |
| 6,080,173 | A | 6/2000 | Williamson, IV et al. | WO | 98/55027 12/1998 |
| 6,083,234 | A | 7/2000 | Nicholas et al. | WO | 99/08603 2/1999 |
| 6,110,188 | A | 8/2000 | Narciso, Jr. | WO | 99/11178 3/1999 |
| 6,113,612 | A | 9/2000 | Swanson et al. | WO | 99/17665 4/1999 |
| 6,117,148 | A | 9/2000 | Ravo et al. | WO | 99/18887 4/1999 |
| 6,120,432 | A | 9/2000 | Sullivan et al. | WO | 99/21491 5/1999 |
| 6,146,393 | A | 11/2000 | Wakabayashi | WO | 99/37218 7/1999 |
| 6,149,681 | A | 11/2000 | Houser et al. | WO | 99/38441 8/1999 |
| 6,152,937 | A | 11/2000 | Peterson et al. | WO | 99/38454 8/1999 |
| 6,152,945 | A | 11/2000 | Bachinski et al. | WO | 99/40851 8/1999 |
| 6,165,185 | A | 12/2000 | Shennib et al. | WO | 99/40868 8/1999 |
| 6,167,889 | B1 | 1/2001 | Benetti | WO | 99/45848 9/1999 |
| 6,171,319 | B1 | 1/2001 | Nobles et al. | WO | 99/52481 10/1999 |
| 6,171,321 | B1 | 1/2001 | Gifford, III et al. | WO | 99/62406 12/1999 |
| 6,176,413 | B1 | 1/2001 | Heck et al. | WO | 99/62409 12/1999 |
| 6,176,864 | B1 | 1/2001 | Chapman | WO | 99/62415 12/1999 |
| 6,186,942 | B1 | 2/2001 | Sullivan et al. | WO | 99/63910 12/1999 |
| 6,187,019 | B1 | 2/2001 | Stefanchik et al. | WO | 99/65409 12/1999 |
| 6,187,020 | B1 | 2/2001 | Zegdi et al. | WO | 00/09040 2/2000 |
| 6,190,396 | B1 | 2/2001 | Whitin et al. | WO | 00/10486 3/2000 |
| 6,190,397 | B1 | 2/2001 | Spence et al. | WO | 00/12013 3/2000 |
| 6,190,590 | B1 | 2/2001 | Randall et al. | WO | 00/15144 3/2000 |
| 6,193,129 | B1 | 2/2001 | Bittner et al. | WO | 00/15146 3/2000 |
| 6,193,734 | B1 | 2/2001 | Bolduc et al. | WO | 00/15147 3/2000 |
| 6,206,912 | B1 | 3/2001 | Goldsteen et al. | WO | 00/15148 3/2000 |
| 6,206,913 | B1 | 3/2001 | Yencho et al. | WO | 00/15149 3/2000 |

FOREIGN PATENT DOCUMENTS

| | | | | |
|---|---|---|---|---|
| EP | 0 701 800 | 3/1996 | WO | 00/27310 5/2000 |
| EP | 0 885 595 | 12/1998 | WO | 00/27311 5/2000 |
| EP | 0 938 870 | 9/1999 | WO | 00/27312 5/2000 |
| EP | 0 820 724 | 1/2000 | WO | 00/27313 5/2000 |
| EP | 0 820 725 | 1/2000 | WO | 00/33745 6/2000 |
| EP | 0 913 125 | 7/2000 | WO | 00/41633 7/2000 |
| EP | 0 990 420 | 12/2000 | WO | 00/53104 9/2000 |
| FR | 2316910 | 4/1977 | WO | 00/56223 9/2000 |
| WO | 92/08513 | 5/1992 | WO | 00/56226 9/2000 |
| WO | 96-25886 | 8/1996 | WO | 00/56227 9/2000 |
| WO | 97/25002 | 7/1997 | WO | 00/56228 9/2000 |
| WO | 97/27898 | 8/1997 | WO | 00/59380 10/2000 |
| WO | 97/31575 | 9/1997 | WO | 00/66007 11/2000 |
| WO | 97/47261 | 12/1997 | WO | 00/66009 11/2000 |
| WO | 98/07399 | 2/1998 | WO | 00/69343 11/2000 |
| WO | 98/19608 | 5/1998 | WO | 00/69346 11/2000 |
| WO | 98/19618 | 5/1998 | WO | 00/69349 11/2000 |
| WO | 98/19625 | 5/1998 | WO | 00/69364 11/2000 |
| WO | 98/19629 | 5/1998 | WO | 00/72764 12/2000 |
| WO | 98/19630 | 5/1998 | WO | 00/74579 12/2000 |
| WO | 98/19631 | 5/1998 | WO | 00/76405 12/2000 |
| WO | 98/19632 | 5/1998 | WO | 01/08601 2/2001 |
| WO | 98/19634 | 5/1998 | WO | 01/12074 2/2001 |
| WO | 98/19636 | 5/1998 | WO | 01/15607 3/2001 |
| WO | 98/30153 | 7/1998 | WO | 01/17440 3/2001 |
| WO | 98/37814 | 9/1998 | WO | 01/19257 3/2001 |
| WO | 98/40036 | 9/1998 | WO | 01/19259 3/2001 |
| | | | WO | 01/19284 3/2001 |
| | | | WO | 01/34037 5/2001 |

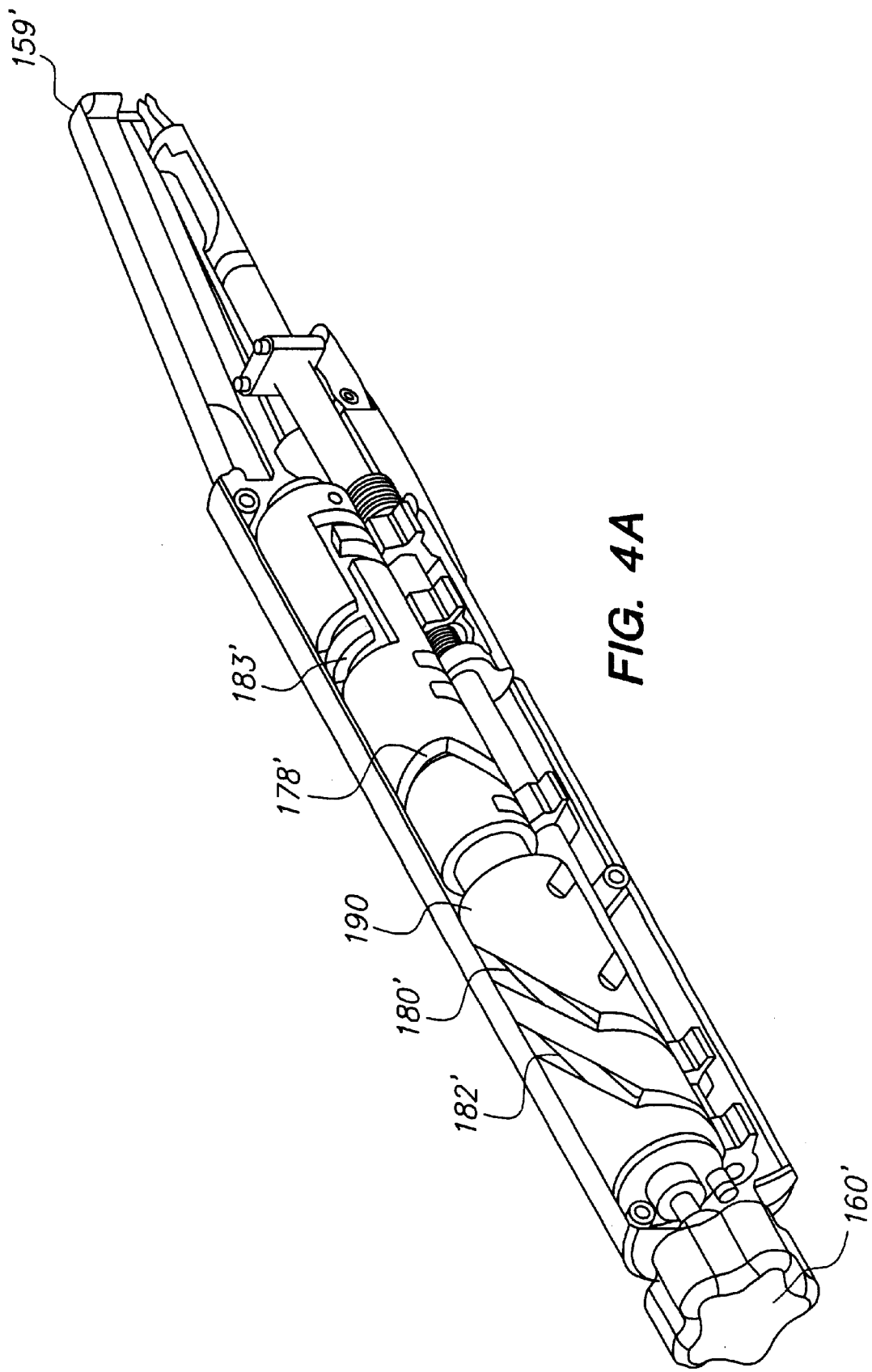

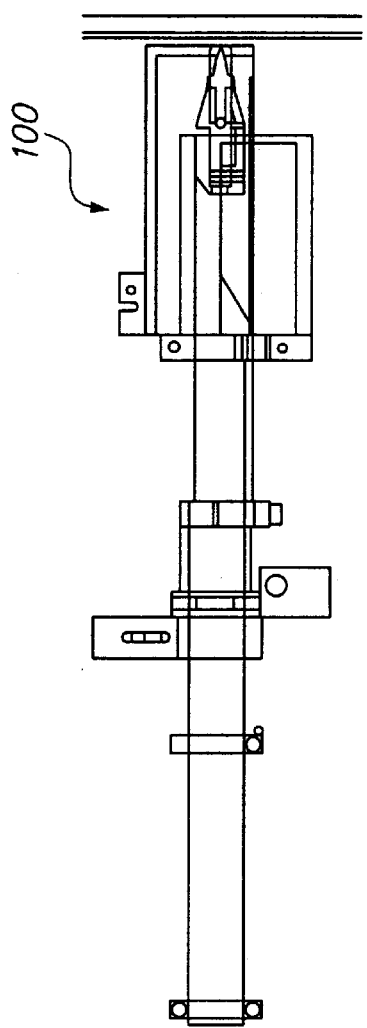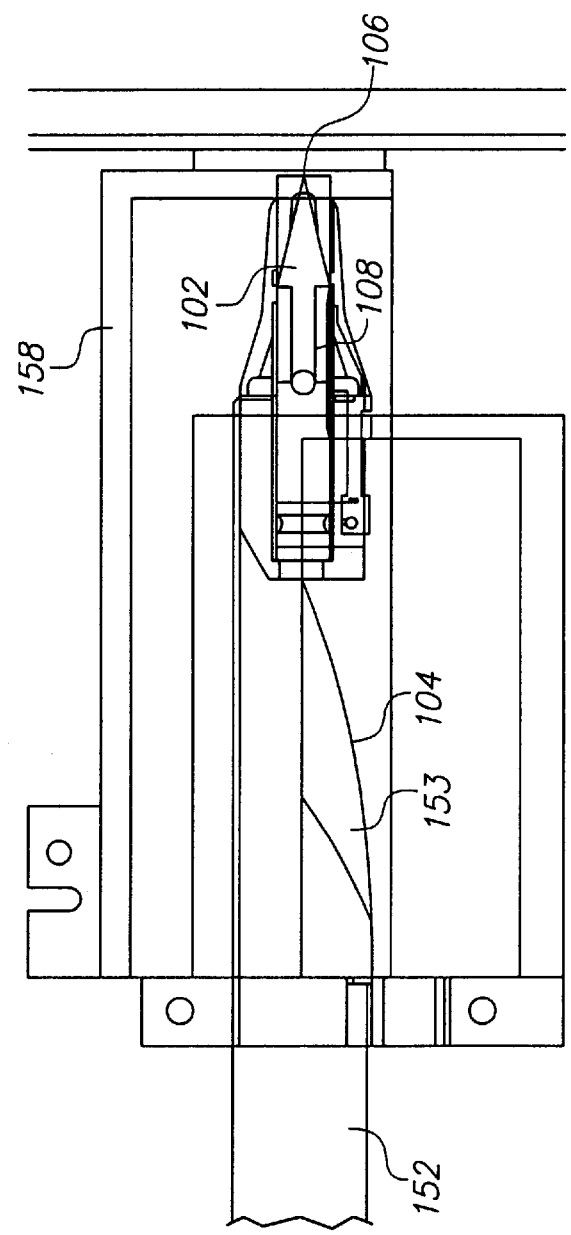
FIG. 5
FIG. 5A

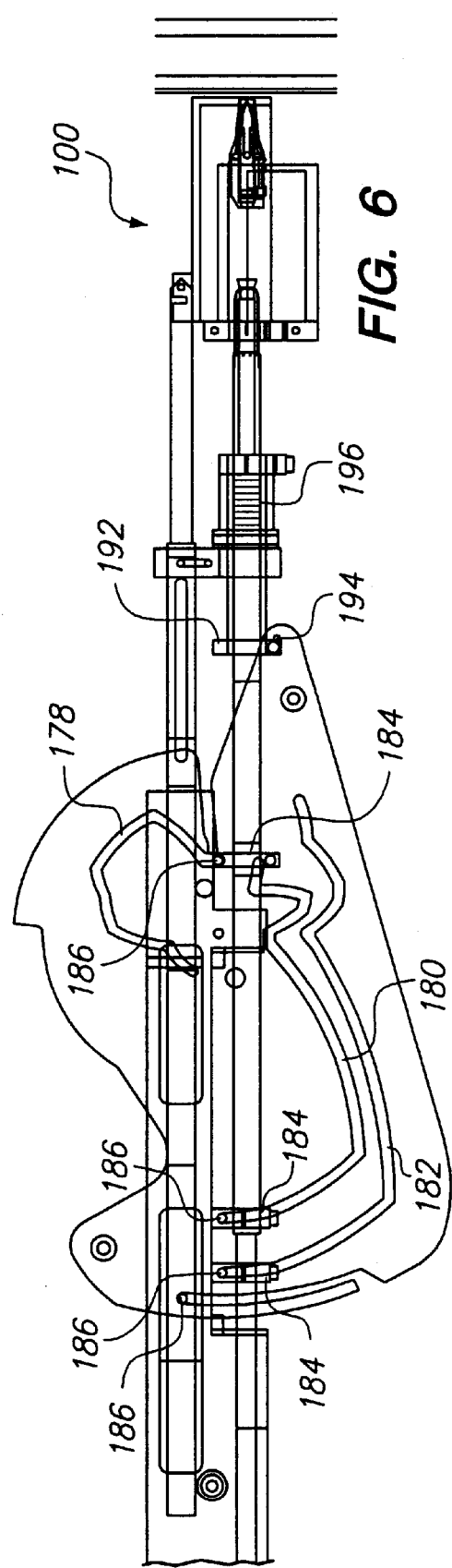
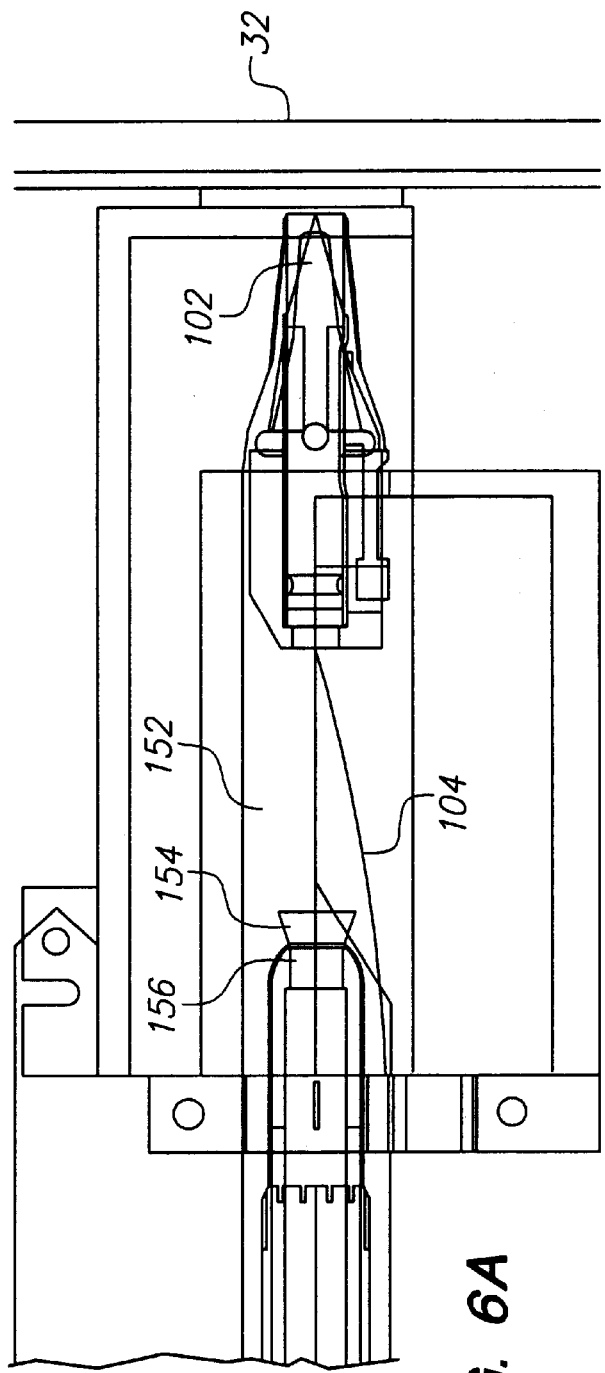
FIG. 6
FIG. 6A

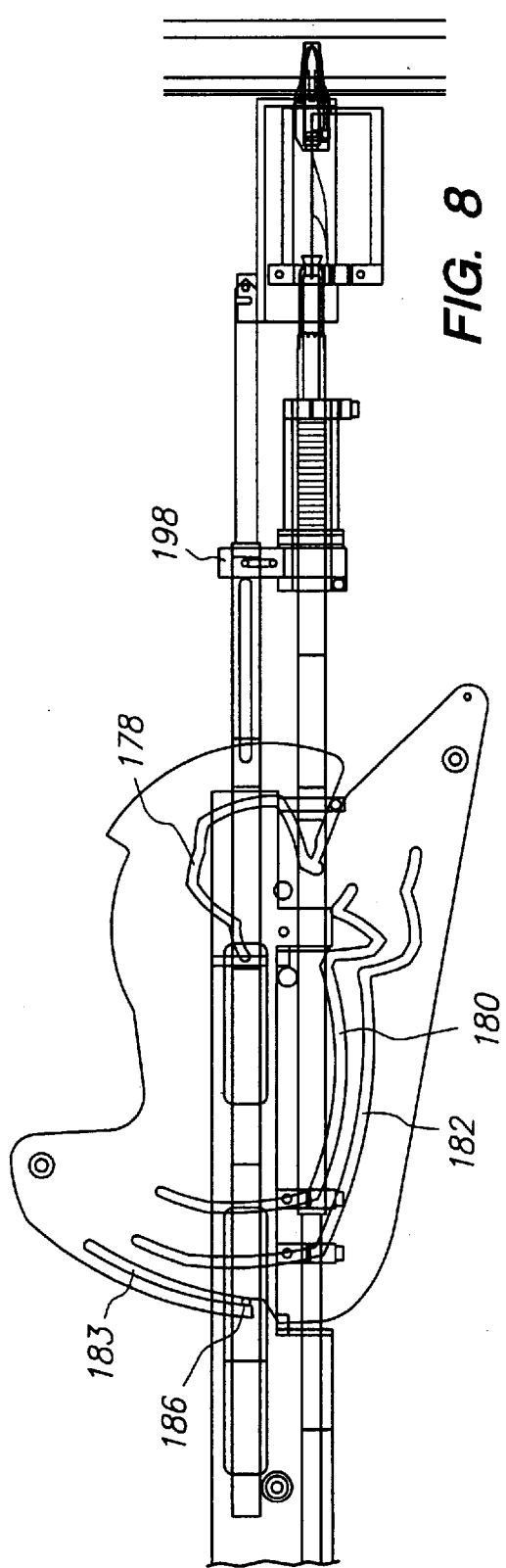
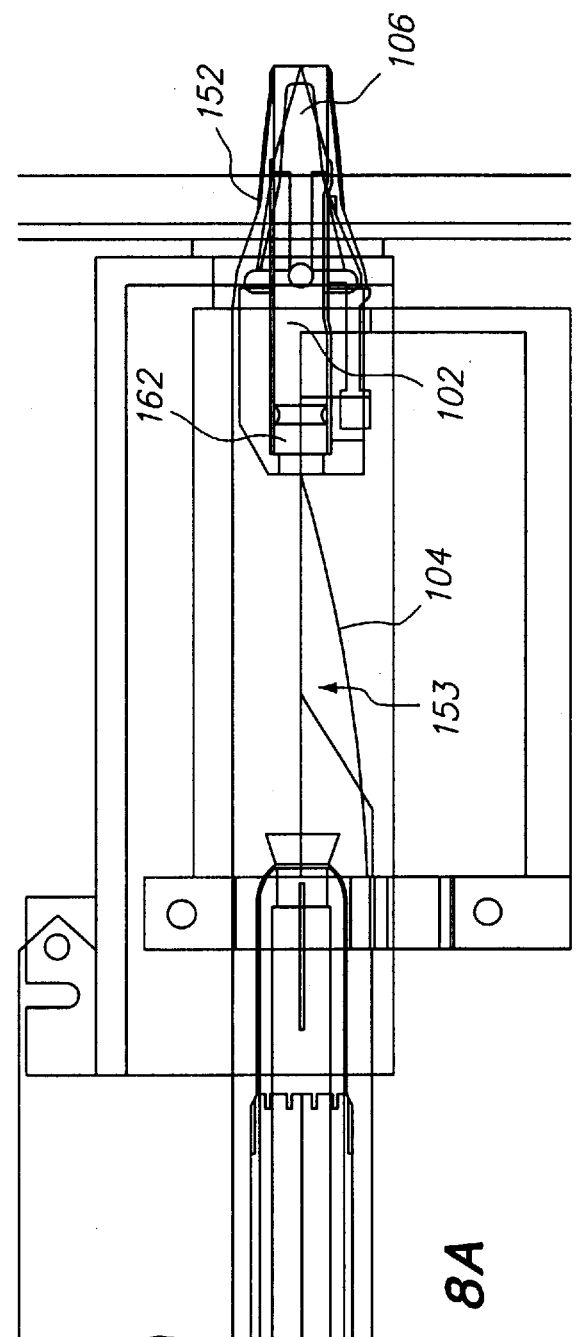
FIG. 8
FIG. 8A

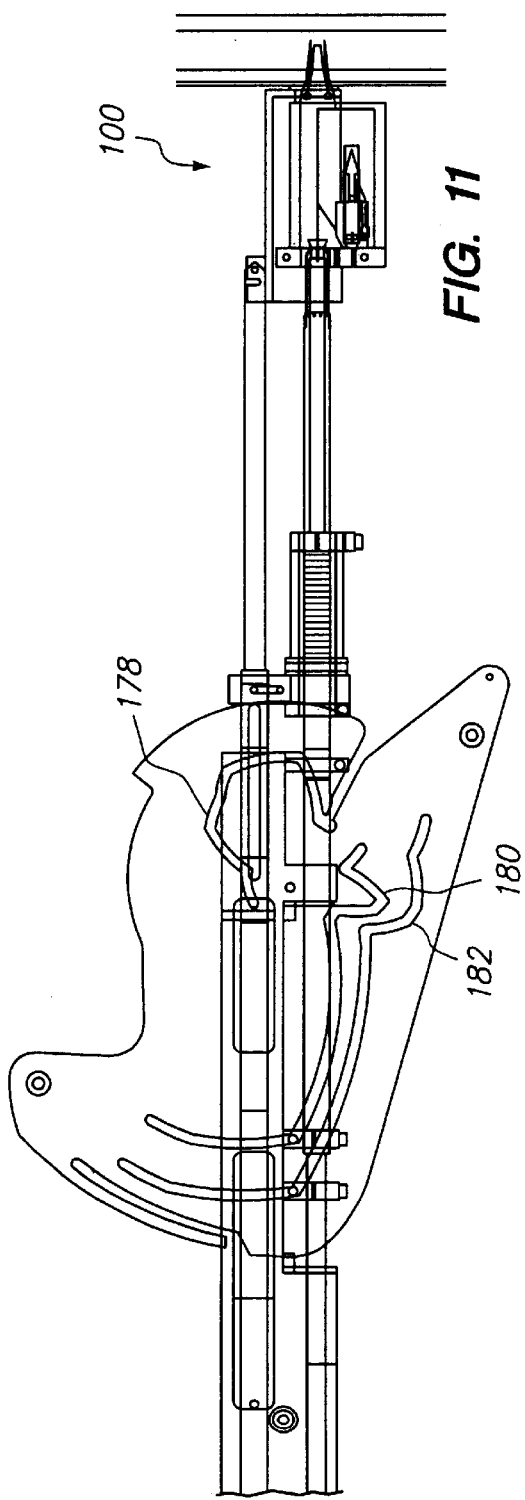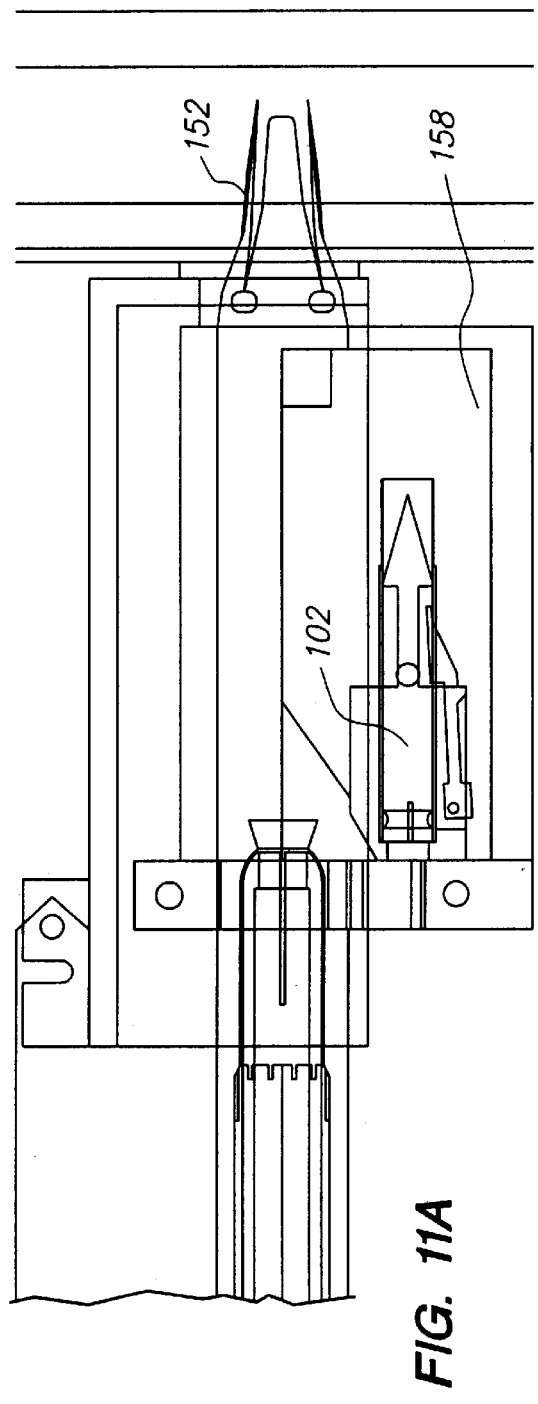

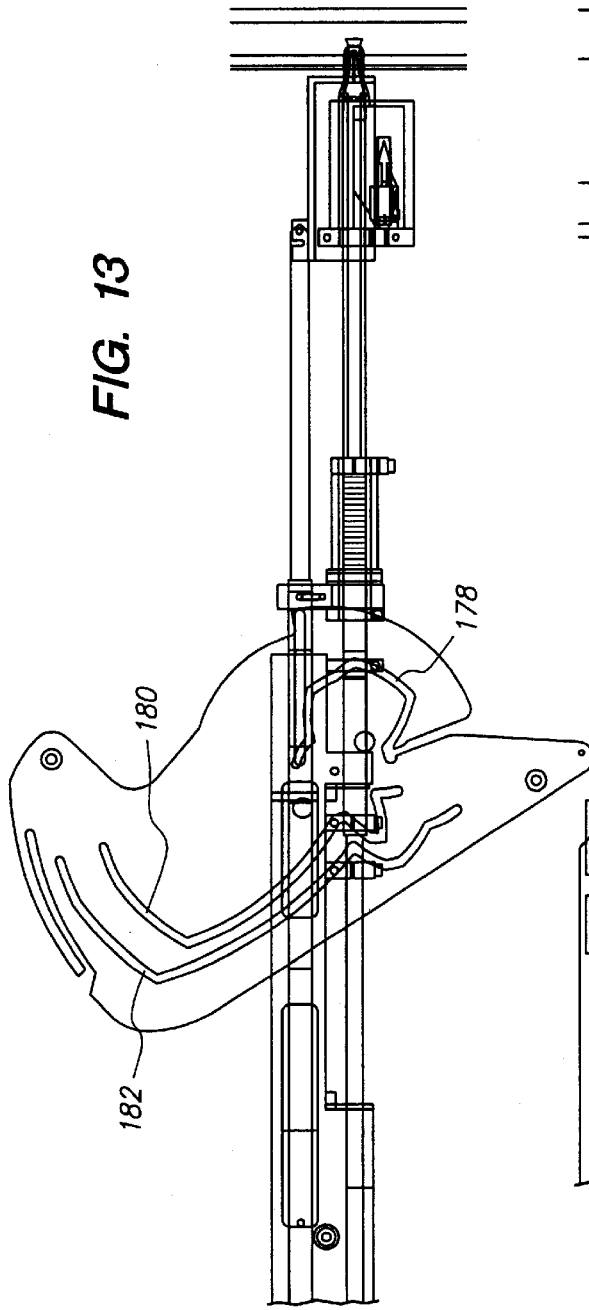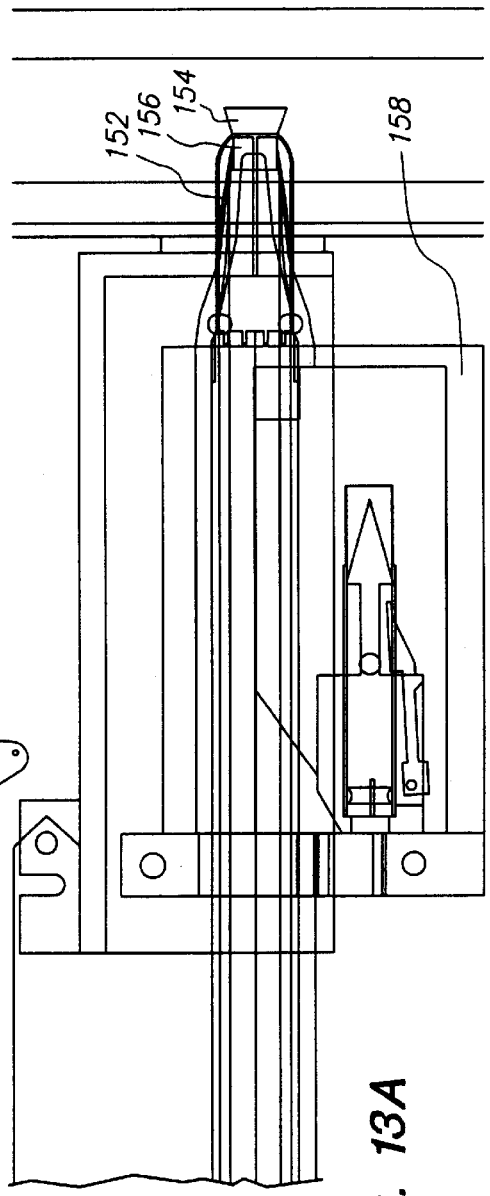

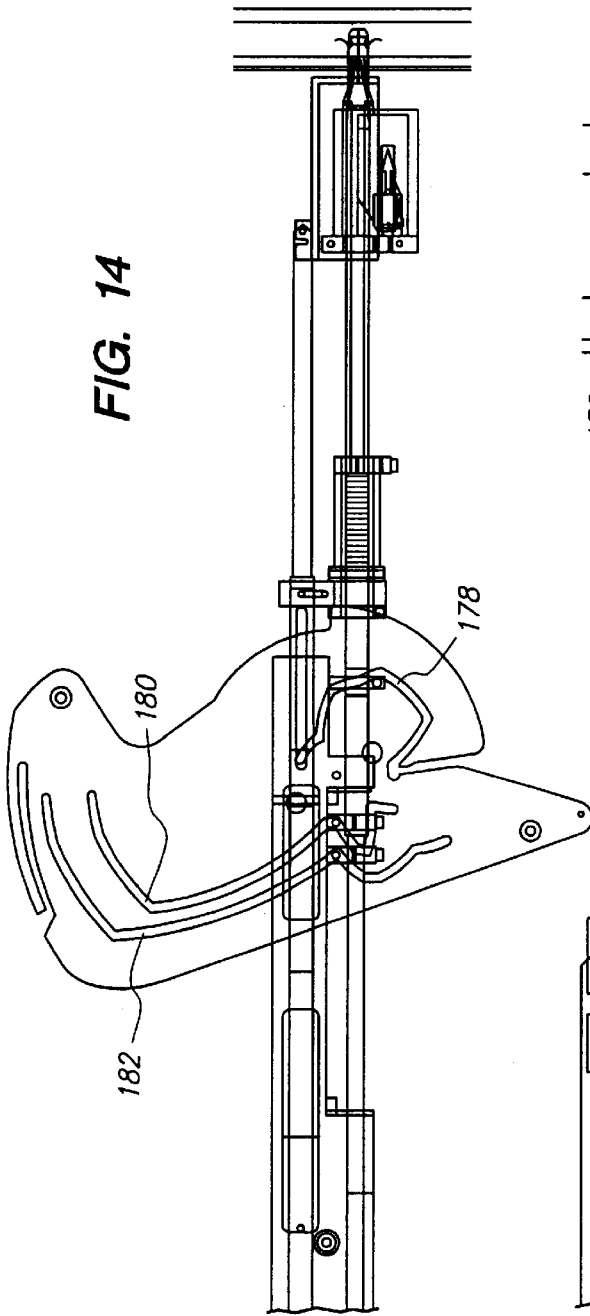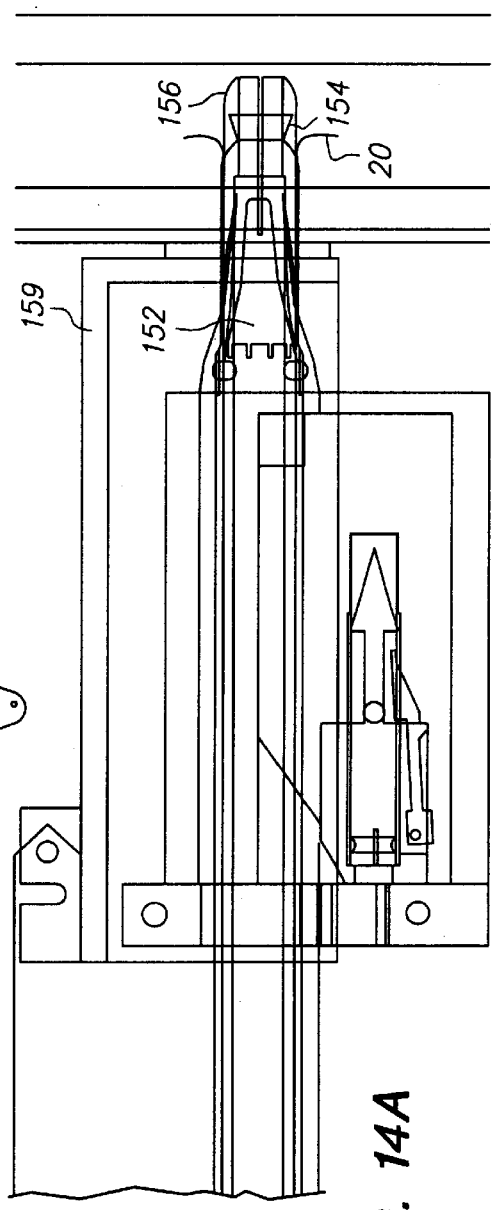
FIG. 14
FIG. 14A

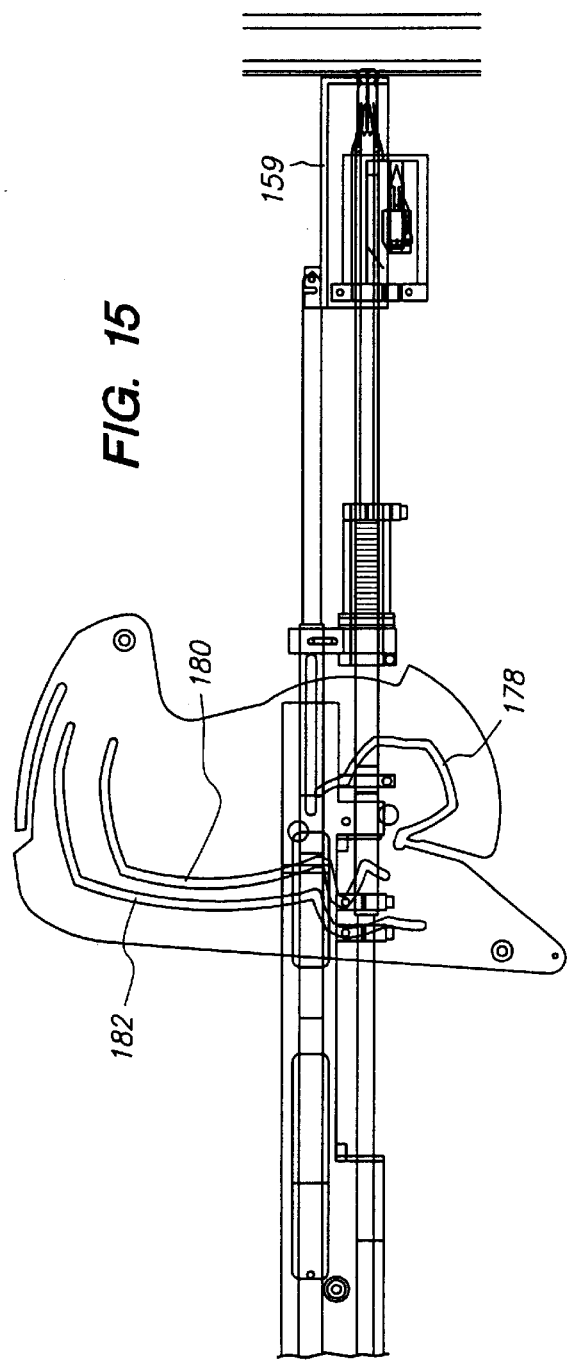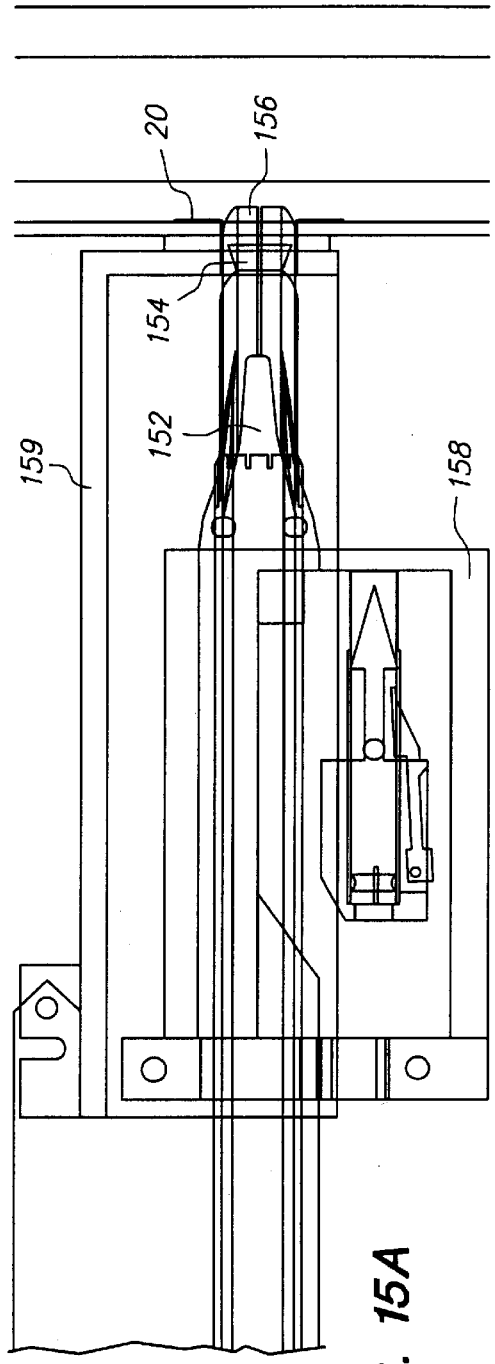

SYSTEM FOR DEPLOYING AN ANASTOMOSIS DEVICE AND METHOD OF PERFORMING ANASTOMOSIS

BACKGROUND OF THE INVENTION

1. Field of the Invention

The invention relates to a system for deployment of an anastomosis device and a method of performing anastomosis. In a preferred embodiment, the system can be used for piercing a vessel wall as an initial step in forming a sutureless connection between a bypass graft and a blood vessel, and the subsequent deployment of an anastomosis device.

2. Brief Description of the Related Art

Vascular anastomosis is a procedure by which two blood vessels within a patient are surgically joined together. Vascular anastomosis is performed during treatment of a variety of conditions including coronary artery disease, diseases of the great and peripheral vessels, organ transplantation, and trauma. In coronary artery disease (CAD) an occlusion or stenosis in a coronary artery interferes with blood flow to the heart muscle. Treatment of CAD involves the grafting of a vessel in the form of a prosthesis or harvested artery or vein to reroute blood flow around the occlusion and restore adequate blood flow to the heart muscle. This treatment is known as coronary artery bypass grafting (CABG).

In the conventional CABG, a large incision is made in the chest and the sternum is sawed in half to allow access to the heart. In addition, a heart lung machine is used to circulate the patients blood so that the heart can be stopped and the anastomosis can be performed. During this procedure, the aorta is clamped which can lead to trauma of the aortic tissue and/or dislodge plaque emboli, both of which increase the likelihood of neurological complications. In order to minimize the trauma to the patient induced by conventional CABG, less invasive techniques have been developed in which the surgery is performed through small incisions in the patients chest with the aid of visualizing scopes. Less invasive CABG can be performed on a beating or stopped heart and thus may avoid the need for cardiopulmonary bypass.

In both conventional and less invasive CABG procedures, the surgeon has to suture one end of the graft vessel to the coronary artery and the other end of the graft vessel to a blood supplying vein or artery. The suturing process is a time consuming and difficult procedure requiring a high level of surgical skill. In order to perform the suturing of the graft to the coronary artery and the blood supplying artery the surgeon must have relatively unobstructed access to the anastomosis site within the patient. In the less invasive surgical approaches, some of the major coronary arteries including the ascending aorta cannot be easily reached by the surgeon because of their location. This makes suturing either difficult or impossible for some coronary artery sites. In addition, some target vessels, such as heavily calcified coronary vessels, vessels having very small diameter, and previously bypassed vessels may make the suturing process difficult or impossible.

An additional problem with CABG is the formation of thrombi and atherosclerotic lesions at and around the grafted artery, which can result in the reoccurrence of ischemia. The thrombi and atherosclerotic lesions may be caused by the configuration of the sutured anastomosis site. For example, an abrupt edge at the anastomosis site may cause more stenosis than a more gradual transition.

Accordingly, it would be desirable to provide a sutureless vascular anastomosis device which easily connects a graft to a target vessel and can be deployed in limited space. It would also be desirable to provide a sutureless anastomosis device which is formed of one piece and is secured to the target vessel by a one piece tool which can perform both the initial piercing of the tissue and deployment of the anastomosis device.

SUMMARY OF THE INVENTION

According to a preferred embodiment, the present invention relates to a deployment system for forming an incision in a wall of a target vessel and delivering an anastomosis device for connecting an end of a graft vessel to a target vessel at the site of the incision. The deployment system preferably includes a trocar, a tissue punch having a piercing element at a distal end thereof for being advanced through the trocar to form a puncture and for thereafter being withdrawn from the trocar, a holder tube slidably disposed within the trocar, an expander tube for cooperating with the holder tube, and a rotatable control, whereby rotation of the control causes advancing and withdrawal of the tissue punch and relative slidable movement between the trocar, the holder tube, and the expander tube for deployment of the anastomosis device. In a further aspect of the invention, the trocar is a tubular member having a passage therein through which the anastomosis device is deliverable to the incision site. Still further, the piercing element comprises a cutting blade which is movable with respect to the trocar such that the cutting blade can be moved from a cutting position at which the cutting blade is exposed to a retracted position at which the cutting blade is not exposed.

According to a further aspect of the present invention, the preferred embodiment is directed to an anastomosis device deployment system including a deployment tool having a rotatable control knob, a holder tube attached to the tool, the holder tube having a distal end configured to hold the anastomosis device with an attached graft vessel, and an expander positioned within the holder and slidable with respect to the holder to a position at which the expander is positioned within the anastomosis device and radially expands the anastomosis device. The system further preferably includes a trocar movable with respect to the holder tube to form an opening in a target vessel to receive the anastomosis device and attached graft vessel. Still further, the deployment tool includes three cam grooves, and the trocar, holder tube and expander each have a follower member engaged in one of the cam grooves to move the trocar, holder tube and expander with respect to one another upon rotation of the control knob.

In accordance with a further embodiment of the invention, a method of performing anastomosis includes providing a deployment tool having a trocar, an expander tube, a holder tube holding a one-piece tubular anastomosis device having an end of a graft vessel everted around the anastomosis device, and a rotatable control knob for moving the trocar, the expander tube and the holder tube relative to one another. The method includes rotating the control knob to puncture a target vessel with the trocar, rotating the control knob to insert the tubular anastomosis device with everted graft vessel into the puncture in the target vessel, rotating the control knob to radial expand the tubular anastomosis device with the expander tube to cause a portion of the anastomosis device to fold outward forming a first annular flange, and rotating the control knob to form a second annular flange on the anastomosis device to trap a wall of the target vessel between the first and second annular flanges and seal the graft vessel to the target vessel. According to a preferred embodiment of the method, enlargement of an internal diameter of the anastomosis device with the expander tube causes the formation of the first flange. According to a further aspect of the invention, the device is expanded by an expander in the form of an inflatable balloon. Still further, in a preferred method of the invention, the radial expansion of the anastomosis device causes a portion of the device to bend at a plurality of hinges to form the first and second annular flanges. The deployment tool may further comprise a tissue punch, wherein rotation of the control knob causes advancement of the tissue punch into the target vessel prior to advancement of the trocar.

Preferably, the target vessel is an aorta and the method is performed without occlusion (i.e., clamping) of the aorta. The end of the graft vessel and the edges of the incision in the target vessel can be captured between the first portion and the second portion so that the end of the graft vessel abuts an outside wall of the target vessel. The anastomosis device can be expandable from a first configuration to a larger second configuration where the anastomosis device is expanded with an expander to cause a portion of the anastomosis device to fold outward forming the first flange. In this regard, the first flange holds a portion of the graft vessel in contact with an inner surface of the target vessel.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 4A is a sectional perspective view of a further embodiment of an anastomosis device deployment tool in accordance with the present invention;

FIG. 5 is a side cross sectional view of a loaded tissue punch device for use in the anastomosis device deployment tool shown in FIG. 3;

FIG. 5A is an enlarged view thereof;

FIG. 6 is a side cross sectional view of the tissue punch device loaded into the anastomosis device deployment tool shown in FIG. 3;

FIG. 6A is an enlarged view thereof;

FIG. 8 is a side cross sectional view of the anastomosis device deployment tool with the trocar moved forward for cutting an opening in the vessel wall;

FIG. 8A is an enlarged view thereof;

FIG. 11 is a side cross-sectional view of the deployment tool with the tissue punch device pivoted entirely out of the trocar;

FIG. 11A is an enlarged view thereof;

FIG. 13 is a side cross-sectional view of the deployment tool with the holder tube and expander tube advanced to begin deployment of the inner flange of the anastomosis device and the trocar beginning to be withdrawn;

FIG. 13A is an enlarged view thereof;

FIG. 14 is a side cross sectional view of the deployment tool with the expander tube advanced to complete deployment of the inner flange of the anastomosis device and the trocar further withdrawn;

FIG. 14A is an enlarged view thereof;

FIG. 15 is a side cross sectional view of the deployment tool with the trocar withdrawn and the expander withdrawn so as to seat the inner flange of the anastomosis device;

FIG. 15A is an enlarged view thereof;

DETAILED DESCRIPTION OF THE PREFERRED EMBODIMENTS

Figure 1:
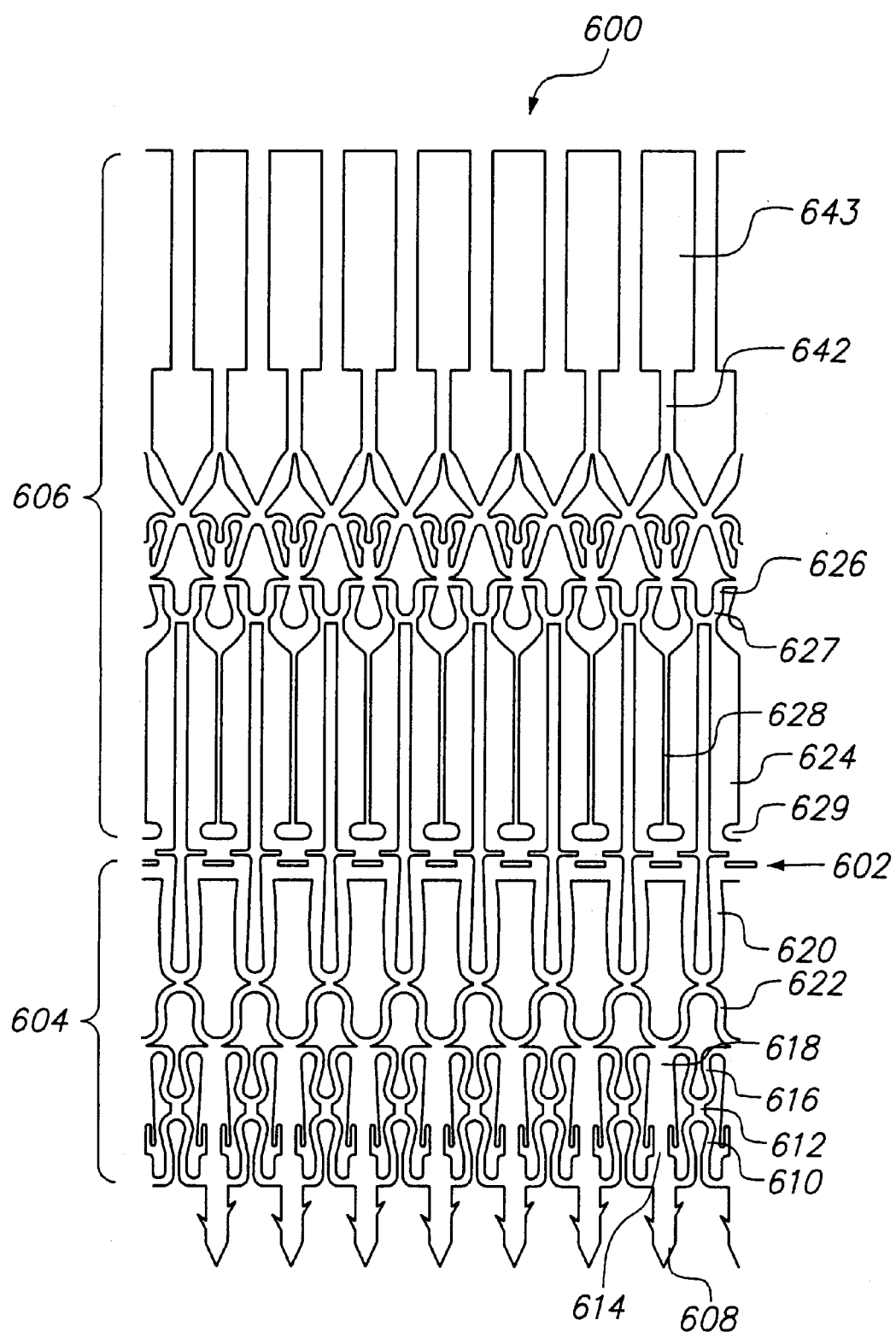
FIG. 1 is perspective views of a typical embodiment of an anastomosis device in a planar configuration.

According to the invention it is possible to perform a variety of anastomosis procedures, including coronary artery bypass grafting. The term "target vessel" is thus used to refer to vessels within the patient which are connected to either or both of the upstream and downstream end of the graft vessel. In such procedures, a large vessel anastomotic device is used with large diameter target vessels such as the aorta or its major side branches.

In deploying a large vessel anastomotic device, the device (with one end of a graft vessel attached thereto) is inserted into an incision in a wall of the target vessel with a deformable section in a first configuration, and the deformable section is radially expanded to a second configuration to deploy a flange. The flange applies an axial force against the wall of the target vessel. Additionally, the flange can be configured to apply a radial force, substantially transverse to the device longitudinal axis, against the wall of the target vessel, to secure the device to the target vessel. For example, the device can have a plurality of deformable sections forming distal and proximal flanges. With the proximal and distal end flanges deployed, the device can be prevented from shifting proximally out of the target vessel or distally further into the interior of the target vessel.

In a coronary bypass operation in accordance with the invention, a device can be used to connect the proximal end of the graft vessel to the aorta. However, in patients with an extreme arteriosclerotic lesion in the aorta, which may result in serious complications during surgical procedures on the aorta, the surgeon may wish to avoid this region and connect the proximal end of the graft vessel to any other adjacent less diseased vessel, such as the arteries leading to the arms or head. Further, the devices can be used with venous grafts, such as a harvested saphenous vein graft, arterial grafts, such as a radial artery, or a synthetic prosthesis, as required.

Connection of the present device does not require the stoppage of blood flow in the target vessel. Moreover, through the use of the device of the present invention, anastomotic devices can be connected to the target vessel without the use of cardiopulmonary bypass, thereby avoiding many of the risks of conventional heart surgery. For example, anastomosis techniques wherein the aorta is clamped to interrupt blood flow to the area of the aortic wall to which a vein is to be anastomosed may result in liberation of plaques and tissue fragments which can lead to organ dysfunction, such as strokes, renal failure, or intestinal ischemia. Further, severely diseased aortas may not provide an area suitable for clamping due to significant calcification of the aortic wall.

According to the invention, a sutureless connection can be provided between a graft and a target vessel, while minimizing thrombosis or restenosis associated with the anastomosis. The anastomotic devices can be attached to the target vessel inside a patient remotely from outside the patient using specially designed applicators, so that the devices are particularly suitable for use in minimally invasive surgical procedures where access to the anastomosis site is limited. The devices allow the anastomosis to be performed very rapidly, with high reproducibility and reliability, without clamping, and with or without the use of cardiopulmonary bypass.

According to one preferred method of deploying the anastomosis device, the surgeon operates a deployment tool using both hands. One hand supports the tool via a handle while the other twists an actuation knob or other control member to deploy the anastomotic device. Locating the actuation knob on the tool's main axis minimizes the tendency of reaction forces to wobble the tool keeping it stable and in proper position during deployment. The twisting motion is converted to linear displacements by a set of rotating cams that engage a trocar, holder, and expander. The cams control the sequence of relative motions between the instrument's trocar and device deployment mechanisms.

During the foregoing procedure, a surgeon will place the tip of the instrument (the mechanical stop) in light contact with the site on the aorta to be anastomosed. Having located a suitable site, the surgeon then twists the actuation knob to fire the spring-loaded tissue punch and continues twisting to continue deployment of the anastomotic device. The trocar penetrates the aortic wall and maintains a substantially fluid-tight seal at the puncture site. Having entered the aortic lumen, the trocar forms a passageway for the anastomotic device and its holder tube (crown) to be advanced, thus retracting the aortic tissue and serving as an introducer for the device. Once the device has fully entered the aortic lumen the trocar begins to be withdrawn, while the anastomotic device is then expanded to its full diameter and an inner flange is deployed. The device is then drawn outwards towards the instrument where a mechanical stop is encounters, and where the inner flange is firmly seated against the intimal wall of the aorta. An outer flange is then deployed from the external side, compressing the aortic wall between the inner and outer flanges, and finally, the device is disengaged from the instrument completing the anastomosis.

Figure 2:
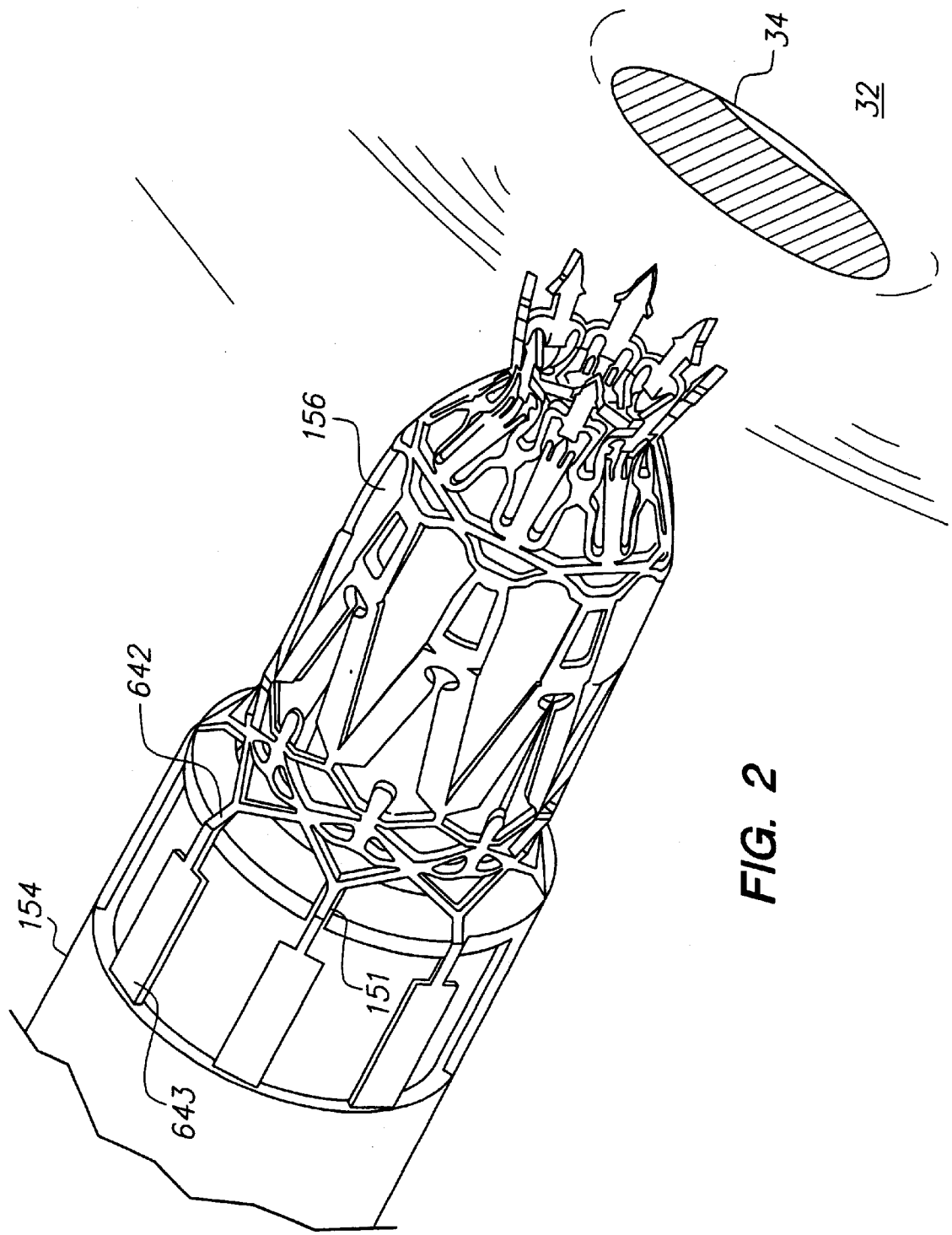
FIG. 2 is a perspective view of the anastomosis device of FIG. 1 in a configuration attached to the deployment tool of the present invention, prior to deployment.

FIGS. 1 and 2 illustrate an exemplary anastomosis device 600 (illustrated in planar form in FIG. 1 for ease of description but which would be used in a tubular shape as shown in FIG. 2) which cooperates with a deployment tool 150 (described below) for delivering and deploying an implant 604 at a site in a living body. The anastomosis device 600 includes a frangible linkage 602 connecting the implant 604 to a discard portion 606. As explained in greater detail below, after the device 600 is positioned at a desired location, the implant 604 can be expanded to deploy an inner flange and subsequently axially compressed to deploy an outer flange while severing the implant 604 from the discard portion 606. The deployment tool can then be withdrawn along with the discard portion 606 which remains attached to the distal end of the deployment tool.

During radial expansion of the device, axially extending barbs 608 are pivoted outwardly by struts 610 such that the outwardly extending barbs 608 and struts 610 form the inner flange. To facilitate bending of the barbs, the barbs 608 comprise points on the ends of axially extending members 612 which have narrow sections 614 located a desired distance from the free ends of the barbs 608. For instance, the narrow sections 614 can be located at axial positions along the device corresponding approximately to a position slightly distal of the axial midpoint of the struts 610 connecting adjacent members 612 when the device is in the preexpanded condition.

To facilitate easier bending of the struts 610 during radial expansion of the device, the distal ends of the struts can be curved at their points of attachment to the members 612. Likewise, a curved bend can be provided at the intersection where the proximal ends of the struts are attached together. When the device is radially expanded, the members 612 move radially outward and circumferentially apart as the struts 610 move radially outward until a force on the barbs 608 by the struts 610 causes the struts to become bent at the narrow sections 614, after which the barbs extend outwardly to form the inner flange. In this deployed condition, the barbs 608 are locked into position by an X-shaped frame formed by struts 610 and additional struts 616. The struts 616 are similar in configuration to the struts 610 with respect to how they are shaped and attached to the members 612. Short axially extending members 618 connect the intersection of the struts 610 to the intersection of the struts 616.

The frangible section 602 is located at the proximal ends of axially extending members 620 which are connected to the members 612 by U-shaped links 622. The members 620 are arranged as circumferentially spaced apart pairs which are attached together at midpoints of links 622. During radial expansion of the device, the individual links 622 are plastically deformed from their U-shaped configuration to form segments of a circumferentially extending annular ring. As a result, the device becomes shorter in the axial direction as links 622 form the annular ring. At the same time, the proximal ends of each pair of members 620 attached to an individual link 622 move radially outward and apart in the circumferential direction.

The frangible section 602 is located between pairs of the axial members 620 and pairs of axially extending members 624. As shown in FIG. 1, the members 620 are substantially parallel to each other when the device is in its unexpanded condition, i.e., prior to formation of the inner flange. However, when the device is radially expanded the distal ends of the members 620 will remain closer together than their proximal ends since the distal ends are attached to a midpoint of the links 622. The proximal ends of pairs of the members 624 are attached at mid-points of U-shaped links 626 by a pair of thin links 627. During expansion of the device, the U-shaped links 626 deform into a circumferentially extending ring while proximal ends of pairs of the members 624 spread apart such that a gap 628 between the pairs of members 624 becomes wider at the proximal ends of the members 624. To aid spreading of the pairs of members 624, the members 624 include a curved recess 629 at the distal ends thereof. The distal ends of members 624 are connected to the proximal ends of the members 620 by a frangible joint comprised of shearable connections 602, the members 620 are connected at their proximal ends by a cross piece 630 and the members 624 are connected by a cross piece 635 which includes a projection 636 received in a recess 634. The frangible joint is formed from a unitary piece of material such as a laser cut tube wherein the shearable connections 602 comprise thin sections of material extending between opposite sides of the projection 636 and opposing walls of the recess 634. When the members 620 and 624 are pivoted to a sufficient extent, the shearable connections 602 are fractured allowing the implant to separate from the discard portion of the device.

Referring also to FIG. 2, the device 600 can be deployed by using a deployment tool 150, described in greater detail below. Briefly, the device 600 includes a crown attached to a distal end of the deployment tool. The crown includes axially extending members 642 with tabs 643 on the proximal ends thereof, the members 642 being held in slots 151 of the tool 150 by the tabs 643. A plastic sleeve (not shown) can be placed over the slots 151 to prevent the members 642 from coming out of the slots. When mounted on the deployment tool with an everted graft vessel thereon (not shown), the crown is flared outwardly such that the members 642 are fully radially expanded at their proximal ends. During radial expansion of the device 600, the diamond shaped linkage of the crown 640 is expanded from an unexpanded condition like the configuration shown in FIG. 1 to an expanded condition having deployed inner and outer flanges.

Although anastomosis device 600 is shown and described for utilization with the deployment system of the present invention, it should be clear to one skilled in the art that other embodiments of such anastomosis devices could of course also be used herewith, including but not limited to, those described for example in U.S. application Ser. Nos. 09/314,278 and 09/437,428, the entire contents of which are hereby incorporated by reference.

Figure 3A:
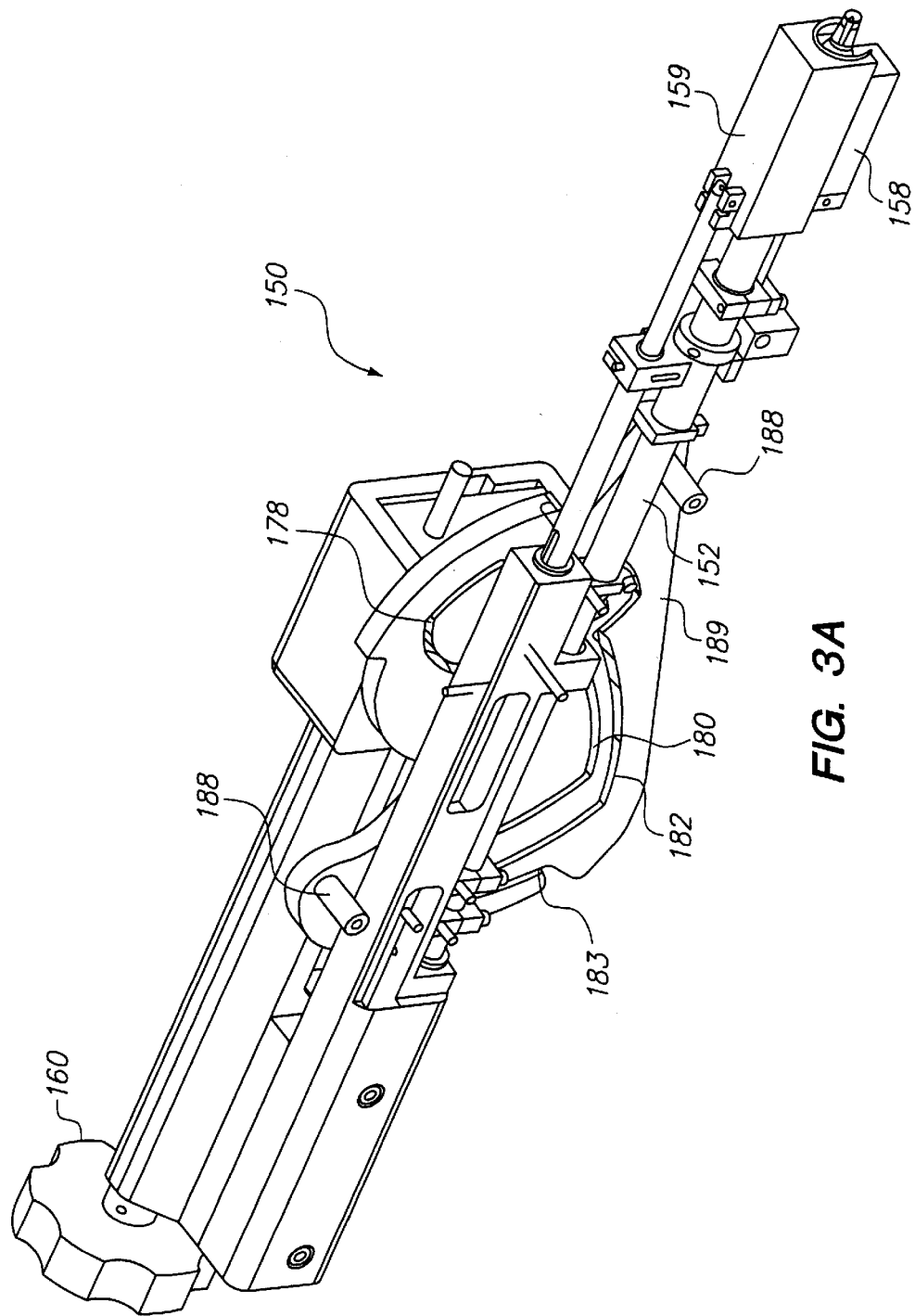
FIG. 3A is a perspective views of an anastomosis device deployment tool in accordance with the present invention.
Figure 3B:
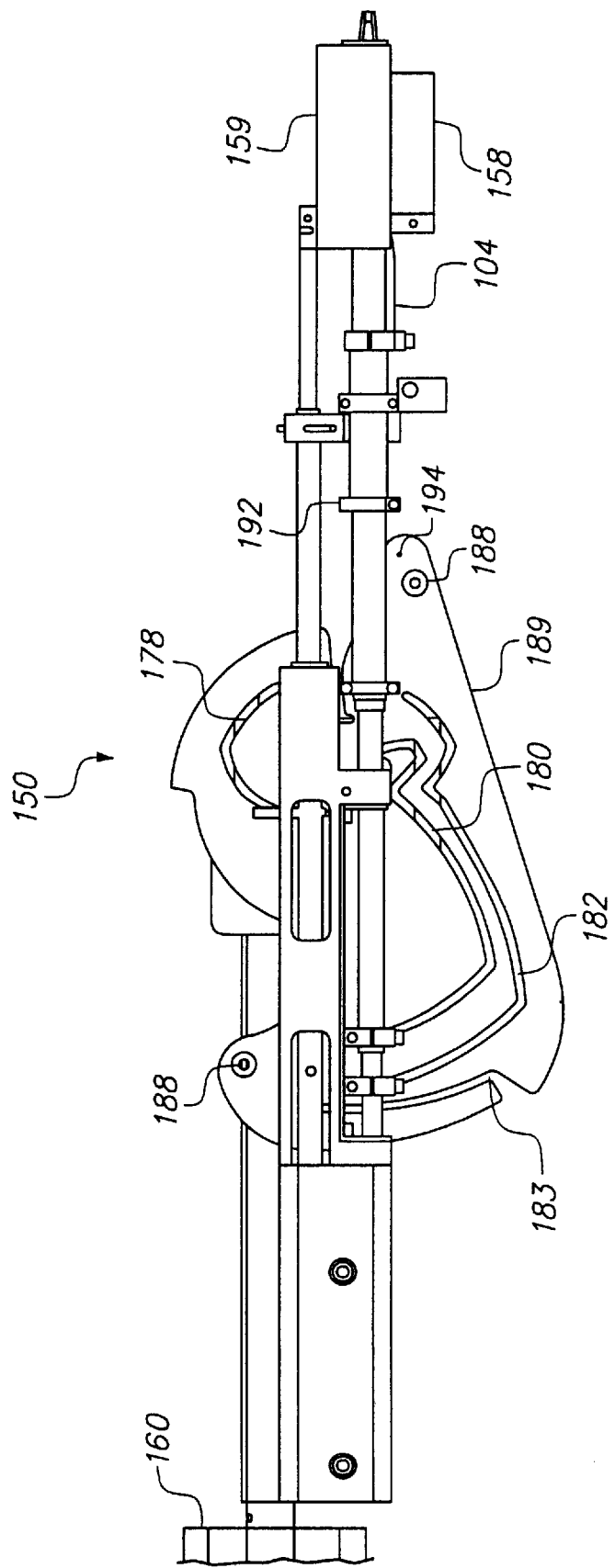
FIG. 3B is a side elevational view thereof.

FIGS. 3A and 3B illustrate the deployment system 150 of the present invention, and the sequential deployment of an anastomosis device 600, including insertion of the anastomosis device past the aortic wall into the aortic lumen, deployment of an inner flange, seating the inner flange on the aortic intima, deployment of the outer flange, seating of the outer flange, and then fixing of the anastomosis device in place and detachment from the tool, is shown in FIGS. 5I–7A. The deployment system 150 includes a hollow outer trocar 152, a holder tube 154 (not shown in FIGS. 3A–3B) positioned inside the trocar 152, and an expandable member or expander tube 156 (not shown in FIGS. 3A–3B) slidably disposed inside of the holder tube 154. As described in detail in the above-mentioned U.S. Ser. Nos. 09/314,278 and 09/437,428, the anastomosis device may be attached to the distal end of the holder tube by inserting members 642 of the device into slots 151 which are formed around the circumference of the holder tube, or by insert-molding, or by any other attachment means. The trocar 152, holder tube 154 and expander tube 156 are all slidable with respect to one another during operation of the device. A control member or device handle 160, preferably a rotatable knob, is provided for moving the tubes with respect to one another through sequential movement of the cams 178, 180, 182, 183 as discussed further below. The device also includes cam connectors 188 which preferably fasten together two halves (shown as a unitary body) which define the cam body 189. The movement of the cams can be caused by mechanical, manual, or pneumatic actuation, as well as any other type of known means for obtaining relative movement. The operation thereof to deploy the anastomosis device 600 according to the present invention is sequentially shown in FIGS. 5–17.

FIGS. 5–5A illustrate a tissue punch 100 in accordance with the present invention, and as more fully described in U.S. application Ser. No. 09/542,976, the entire contents of which is hereby incorporated by reference. As illustrated, the tissue punch 100 is loaded and ready for attachment to the deployment system 150. The tissue punch 100 includes a piercing element 102 positioned within the trocar 152. The piercing element 102 can be retracted in the trocar 152 by an elongated member 104, such as a spring steel strap or cable which extends through an opening 153 in a side of the trocar 152. The piercing element 102 includes a pointed distal tip 106 for penetrating the target vessel wall 32 and a narrow shaft portion 108 around which the tissue of the target vessel wall 32 contracts after piercing. The deployment system of the present invention further includes a mechanical stop 159 which is preferably compliant in nature in that it may be spring loaded and which will abut the outer wall surface of the aorta during the anastomosis procedure. The spring loading on the stop 159 is preferably in the range of approximately 0.5 to 3.0 pounds. As shown in FIG. 5A, the mechanical stop has been located against the wall of the aorta and will be locked in said position by the cam rotation to function as a reference point for locating the outer wall of the aorta during further operation of the deployment tool 150.

Figure 4B:
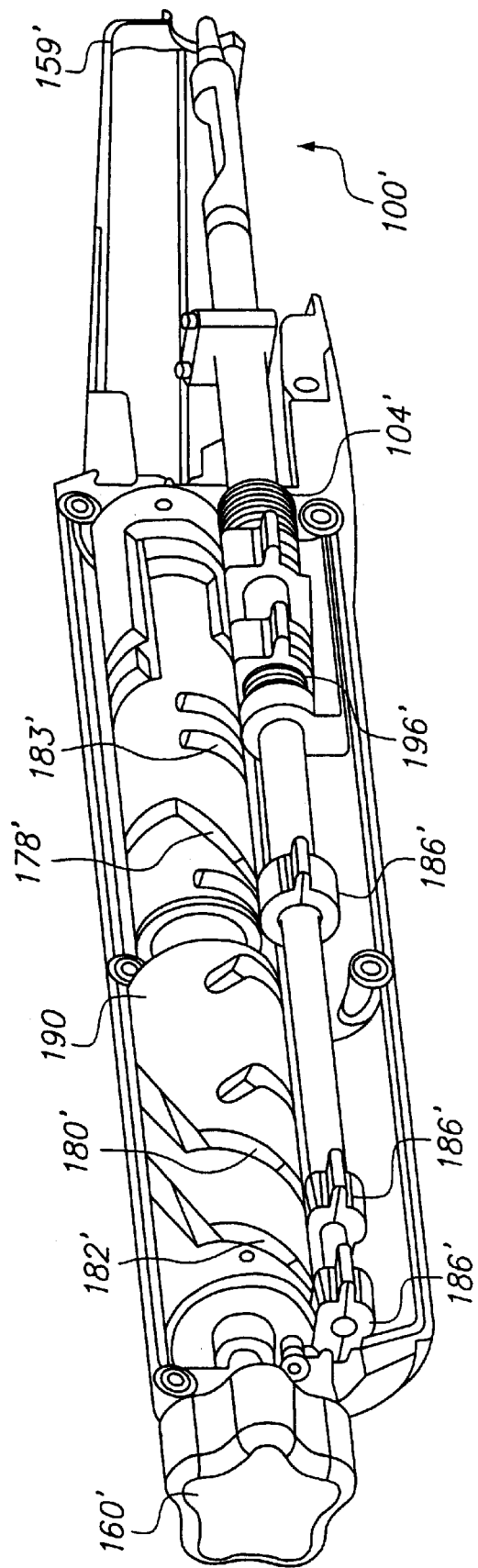
FIG. 4B is a side elevational view thereof.

FIGS. 6–6A illustrate the tissue punch 100 attached to the deployment tool 150. The deployment tool 150 preferably includes a cam body 189 having four contoured cam slots 178, 180, 182, 183 corresponding to the trocar 152, holder tube 154, expander tube 156, and a retraction release mechanism for the tissue punch 100, respectively. Each of the tubes has a fitting 184 at a distal end thereof. An engagement member or pin 186 connected to each of the fittings 184 slides in a corresponding one of the cam slots 178, 180, 182, 183. Alternatively, it is within the scope of the present invention to provide the deployment tool with additional or fewer cam slots. Still further, in accordance with a further embodiment of the invention as shown in FIGS. 4A and 4B (prime reference numerals being used to denote similar features) the cam grooves 178', 180', 182', 183' may be formed in one or more rotatable cylinders 190 and engagement members 186' are provided for engagement within the grooves. A spring 196' is provided which, upon release during the initial rotation of the knob 160', results in firing of the piercing element 102 of the tissue punch 100'. A further spring 104' is provided for retraction of the tissue punch upon the release thereof during subsequent rotation of the control member 160', as discussed further below with respect to the first embodiment of the invention. In both embodiments of the present invention, as the knob 160 is rotated, the engagement members slide in the respective cam slots or grooves to cause corresponding rotation of the cams and to cause actuation and retraction of the tissue punch and to move the trocar, holder tube and expander tube to the successive positions illustrated in FIGS. 5–17, and deploy the anastomosis device, as explained in detail below with respect to the first embodiment of the invention. A gear box may also be utilized to obtain the desired correspondence between rotation of the control member and the corresponding rotation of the cams. As shown in FIG. 6, a trigger pin 194 is engaged with a collar 192 of the tissue punch 100 so as to prevent the inadvertent firing of the piercing element prior to release. A spring 196 is also shown in its compressed state awaiting release of the trigger pin 194.

Figure 7:
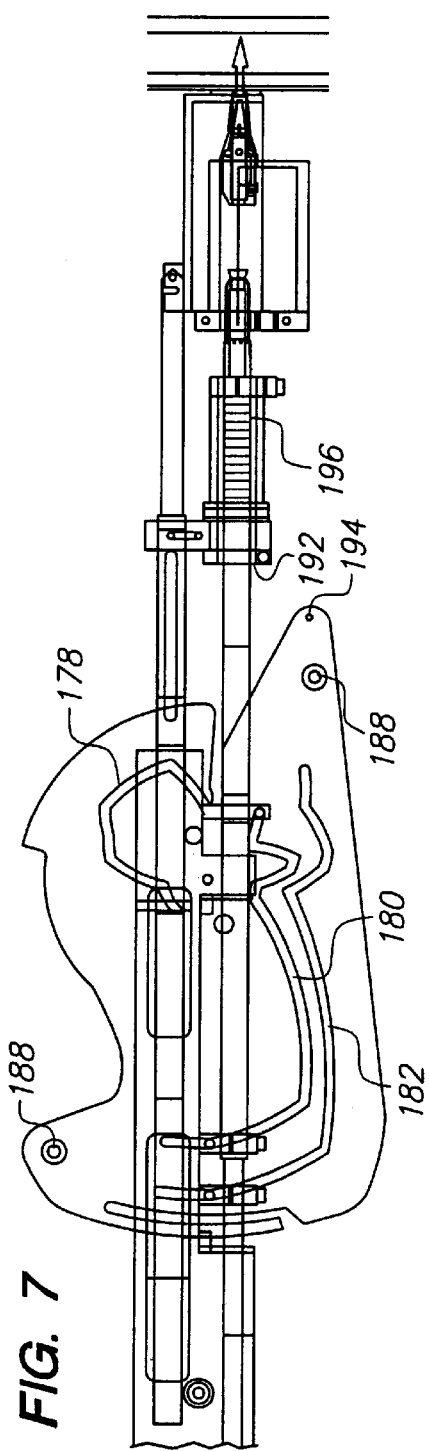
FIG. 7 is a side cross sectional view of the anastomosis device deployment tool with the piercing element puncturing the target vessel.
Figure 7A:
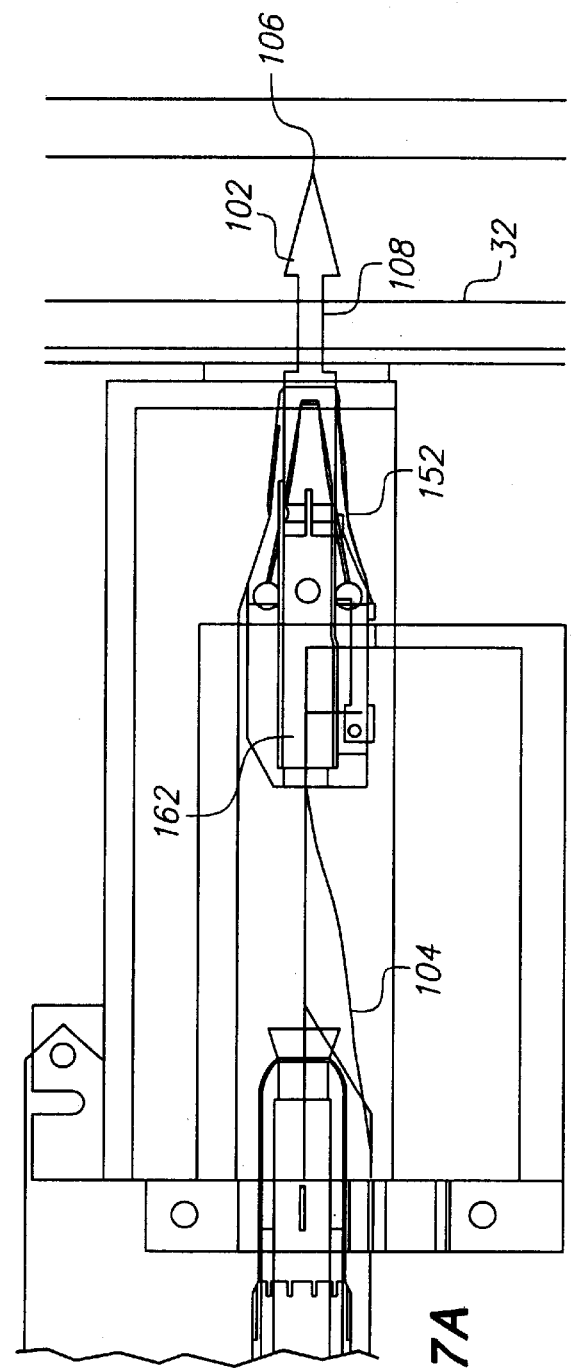
FIG. 7A is an enlarged view thereof.

Upon rotation of the knob 160 by the surgeon, thereby obtaining rotation of the cams as shown in FIG. 7, the trigger pin 194 releases the collar 192 and the compressed spring 196. The piercing element 102 of the tissue punch 100 is thus advanced by the spring actuation into the wall of the target vessel 32, as shown in the enlarged view of FIG. 7A, while the trocar 152 remains within the housing 158. After piercing, the tissue of the target vessel wall rests around the shaft portion 108 of the piercing element 102.

Referring to FIGS. 8 and 8A, the knob 160 has been further rotated as evidenced by the further rotated position of the cams 178, 180, 182, 183, and the trocar 152 and tissue punch sheath 162 have been advanced through the target vessel wall to thereby capture the piercing element 102 within the sheath 162 and punch the required opening 34 in the target vessel 32. The tissue surrounding the shaft 108 is severed from the vessel wall and trapped within the sheath 162 for excision. As illustrated, the pin 186 is disposed at the terminal edge of cam slot 183, just prior to release of the tissue retraction mechanism 198.

Figure 9:
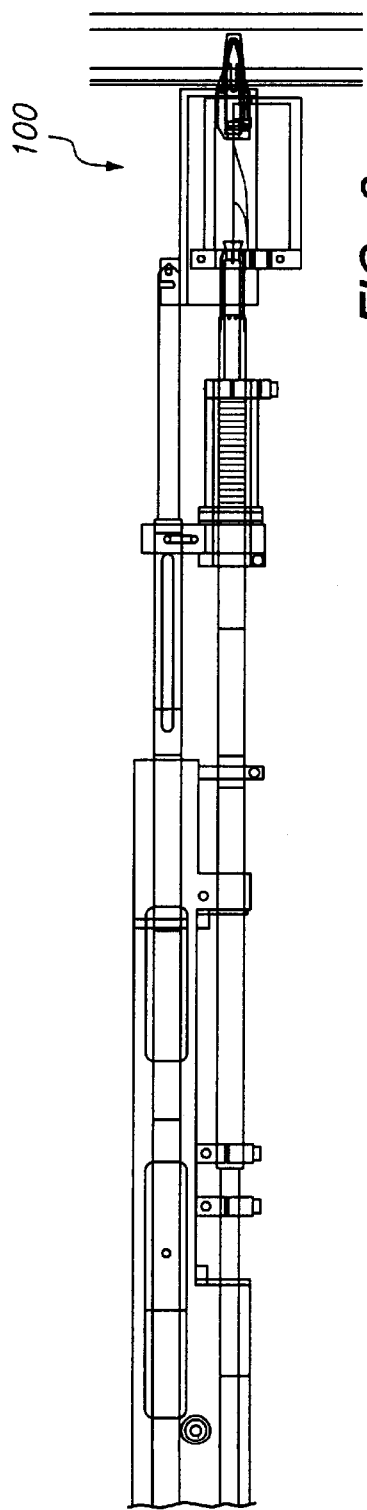
FIG. 9 is a side cross-sectional view of the deployment tool when the tissue punch spring has fired.
Figure 9A:
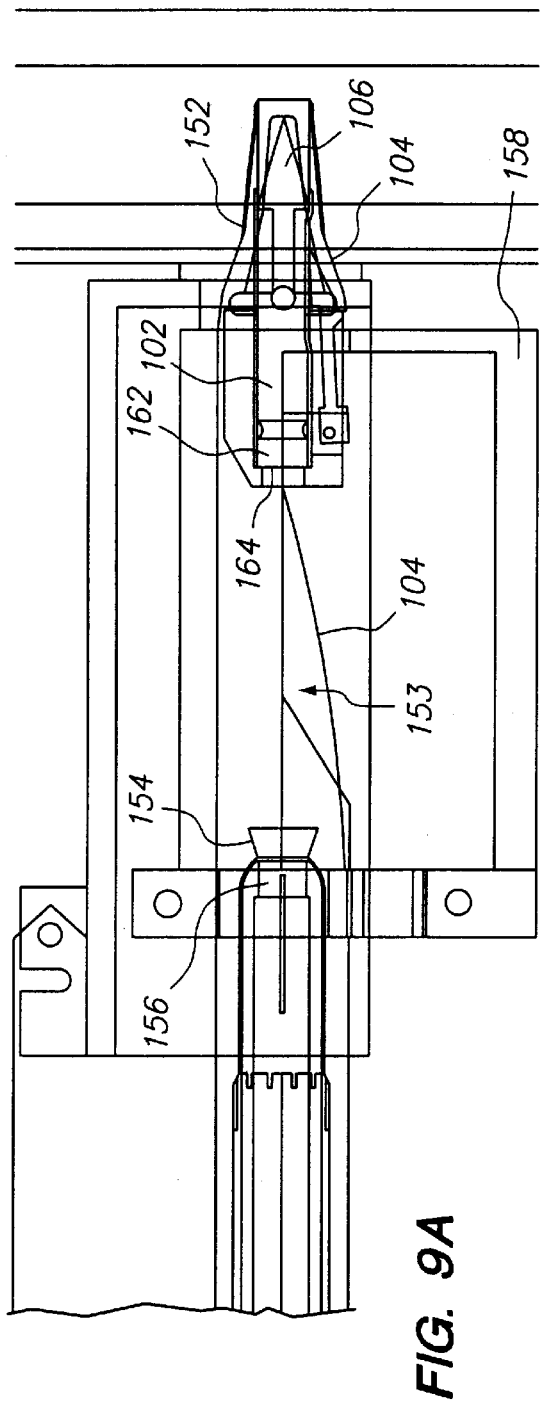
FIG. 9A is an enlarged view thereof.
Figure 10:
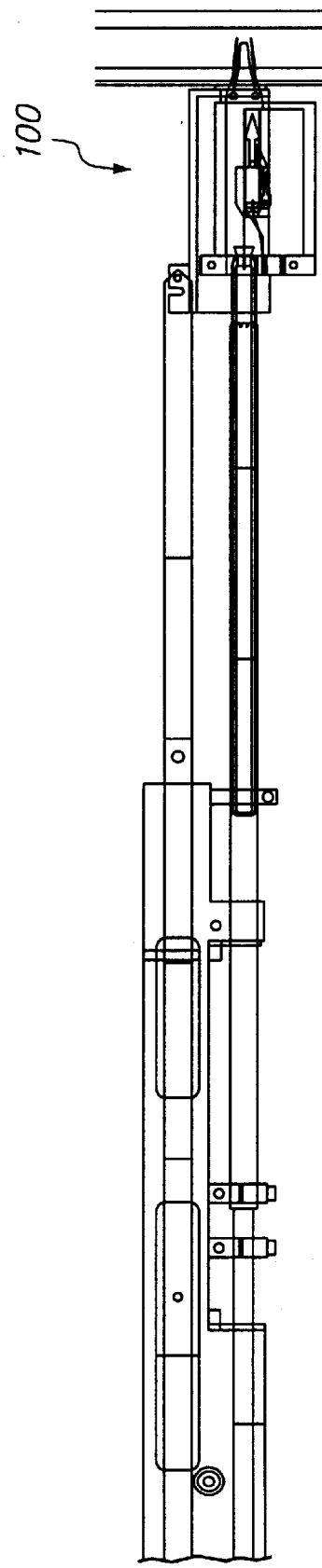
FIG. 10 is a side cross-sectional view of the deployment tool as the tissue punch is being withdrawn through the opening in the side of the trocar.
Figure 10A:
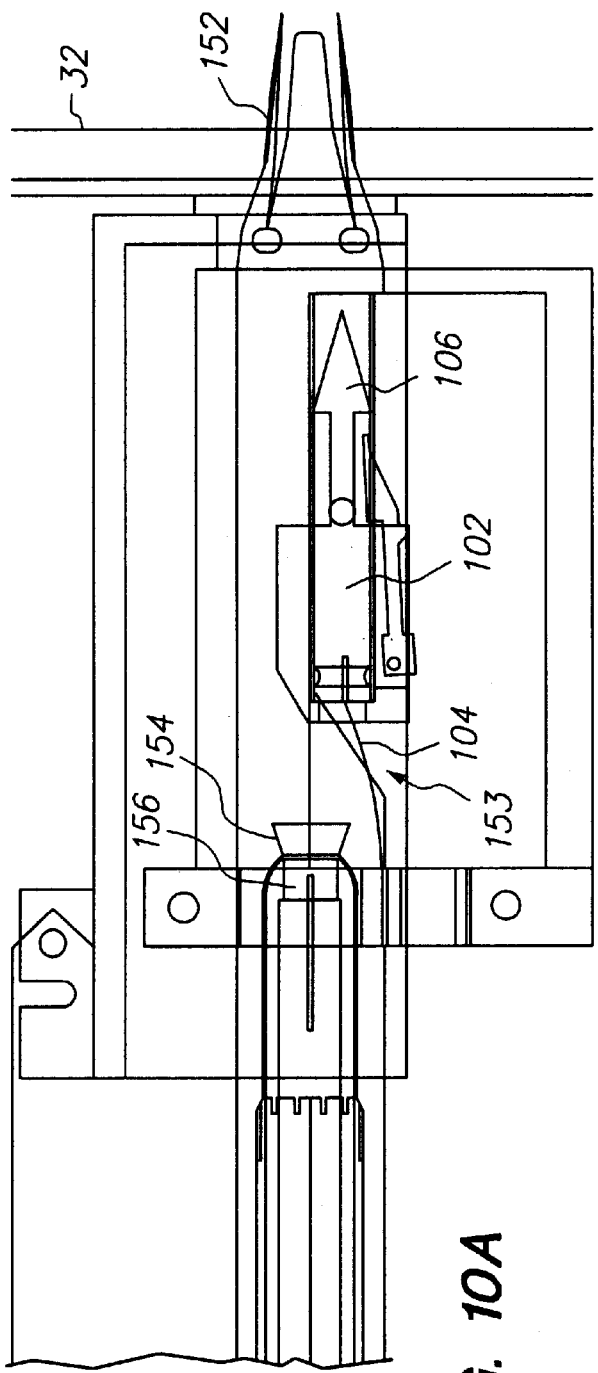
FIG. 10A is an enlarged view thereof.

FIGS. 9–11A illustrate the retraction of the tissue punch 100 upon successive rotation of the knob 160 and the corresponding rotation of the cams following the release of pin 186 from cam slot 183. In FIG. 9A, the retraction spring 104 has been actuated and the piercing element 102 is withdrawn such that it bottoms on a rear surface 164 of the sheath 162. Further retraction of the tissue punch 100, as shown in FIG. 10A, causes the tissue punch to rotate out of the opening 153 in the trocar 152. As shown in FIG. 11A, the tissue punch 100 continues to rotate to a storage position outside of the trocar 152 within the housing 158. When the tissue punch 100 is in the storage position, the lumen within the trocar 152 can be used to maintain the opening 34 within the blood vessel and for delivery of the anastomosis device to the puncture site in the target vessel.

Figure 12:
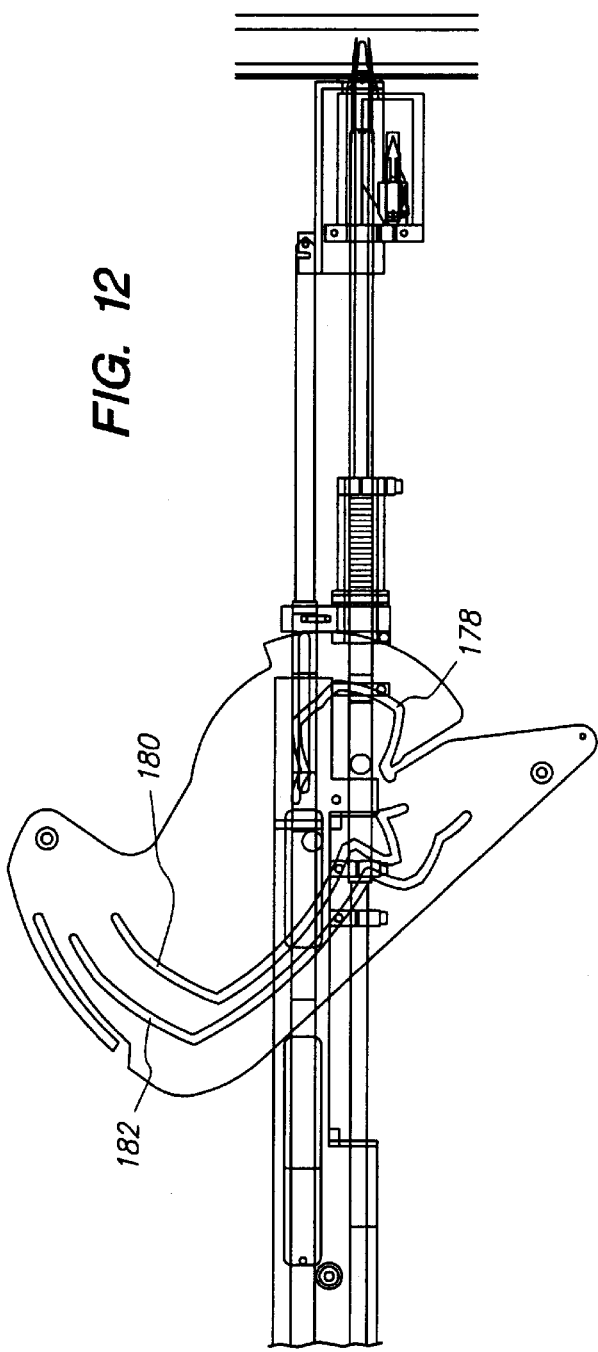
FIG. 12 is a side cross-sectional view of the deployment tool with the holder tube and expander tube moved forward for the deployment of the anastomosis device.
Figure 12A:
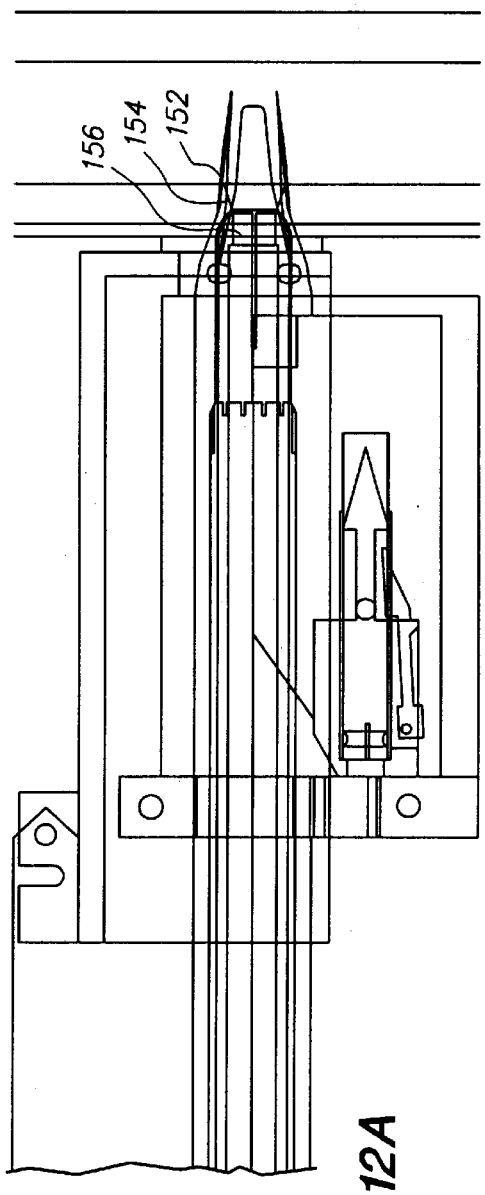
FIG. 12A is an enlarged view thereof.

Further rotation of the knob 160 brings the cams 178, 180, 182 to the rotated position shown in FIG. 12. In so doing, the holder tube 154 with the anastomosis device 600 attached thereto has been shuttled forward to the puncture site along with the expander tube 156, while the trocar 152 has begun to withdraw.

Referring to FIGS. 13–13A, the cams have been further rotated. Moreover, the holder tube 154 has advanced to within the target vessel with the anastomosis device 600 attached thereto. The expander tube 156 is immediately behind the holder tube 154 prior to deployment of the anastomosis device 600, while the trocar 152 has further withdrawn within through the opening 34. The anastomosis device 600 is now in position for deployment. More particularly, due to the variation in the thickness of the aortic wall among patients, the holder tube is advanced significantly past, approximately 0.2 inch for example, a position which would be required for the thickest possible aortic wall such that the surgeon can be certain that the anastomosis device is within the lumen of the target vessel and the inner flange will thus be deployed intramurally, as described below.

FIGS. 14–14A show the cams further rotated by the knob 160 and the cam slot 182 has caused the expander tube 156 to be advanced through the holder tube 154 to thereby deploy the inner flange 20 of the anastomosis device. Although an expander tube is preferable for causing the deployment of the inner flange, it is within the scope of the present invention to use other mechanisms for causing the deployment thereof. The trocar 152 has also been further withdrawn from the puncture site.

FIGS. 15–15A show that further rotation of the knob 160 causes the further pivoting of the cams 178, 180, 182. As shown in FIG. 15A, the holder tube 154 and the expander tube 156 have been slightly withdrawn to pull the inner flange of the anastomosis device 600 against the vessel wall 32. The trocar 152 is also now completely withdrawn into the housing 158. Because of the variation in the thickness of the aortic wall among patients, the retraction of the inner flange is overshot beyond that which would be required for the thinnest possible aortic wall. In so doing, the present invention ensures that the inner flange will be in firm contact with the inner surface of the aortic wall. The mechanical stop 159 is released from its locked reference point during seating of the inner flange, and the compliant nature thereof allows the stop 159 to thus function as a counter-force against the withdrawal of the holder tube and expander tube and the retraction of the inner flange. An alternative embodiment to the mechanical stop may not be spring loaded, but rather, may include a larger outer diameter on the distal end thereof. As such, the mechanical stop will cause the surrounding tissue to stretch and thus provide a certain degree of resiliency which can adequately counteract the withdrawal force during the seating of the inner flange.

Figure 16:
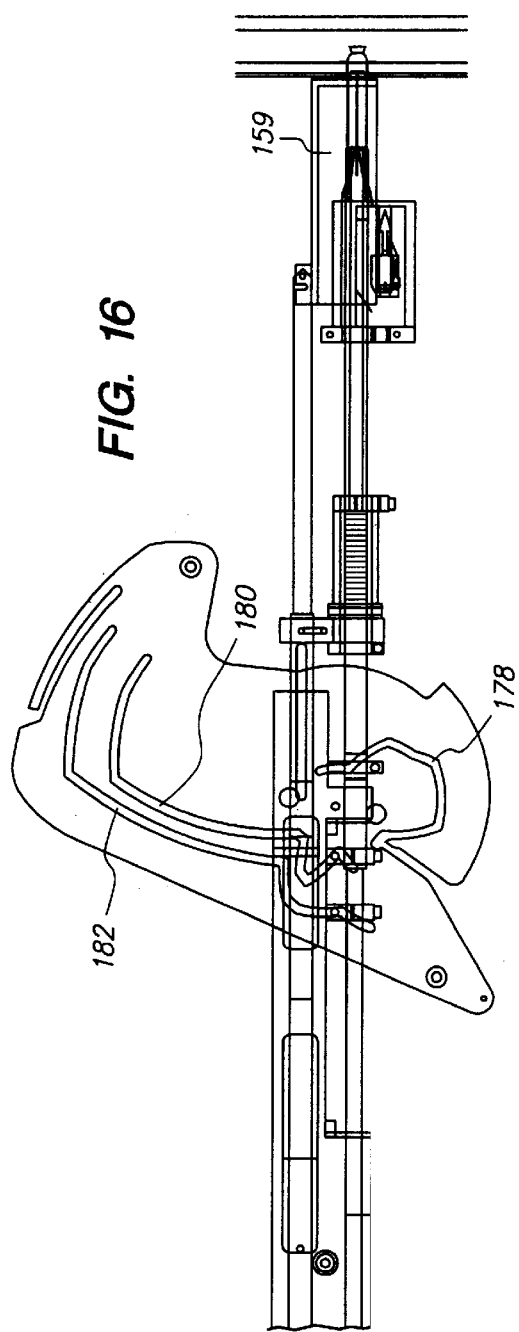
FIG. 16 is a side cross sectional view of the deployment tool with the holder tube advanced for deployment of the outer flange of the anastomosis device and disengagement of the anastomosis device therefrom.
Figure 16A:
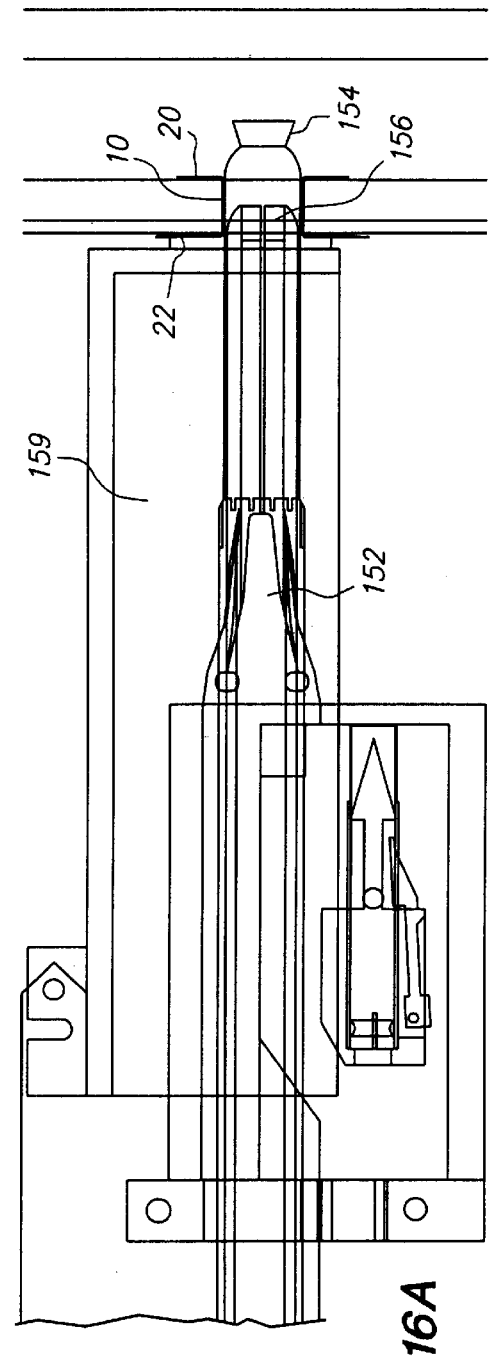
FIG. 16A is an enlarged view thereof.

As shown in FIGS. 16–16A, the cams have been further pivoted due to the successive rotation of the knob 160, and in so doing the holder tube 154 has moved forward again to deploy the outer flange 22 of the anastomosis device through compression of the linkages, and disengage the holder tube 154 from the anastomosis device 600. The inner and outer radial flanges 20, 22 trap the wall of the target vessel 32 between the flanges and thus secure the everted graft vessel 30 to the target vessel. In this instance, the mechanical stop 159 abuts the outer wall surface of the aorta during the deployment of the outer flange and prevents the unseating of the inner flange.

Figure 17:
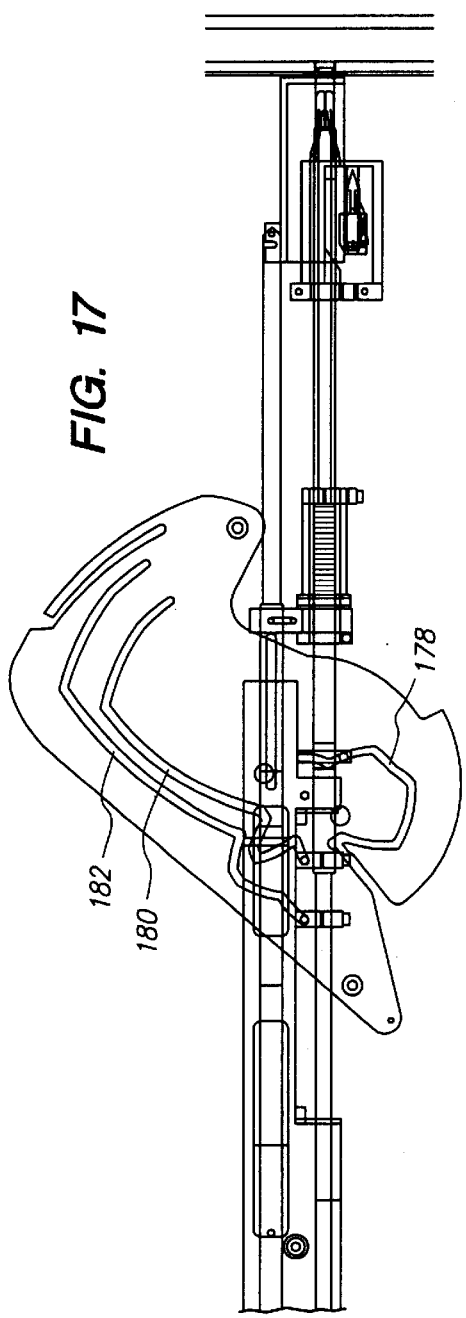
FIG. 17 is a side cross sectional view of the deployment tool with the trocar, expander tube and holder tube withdrawn for tool removal from the target vessel.
Figure 17A:
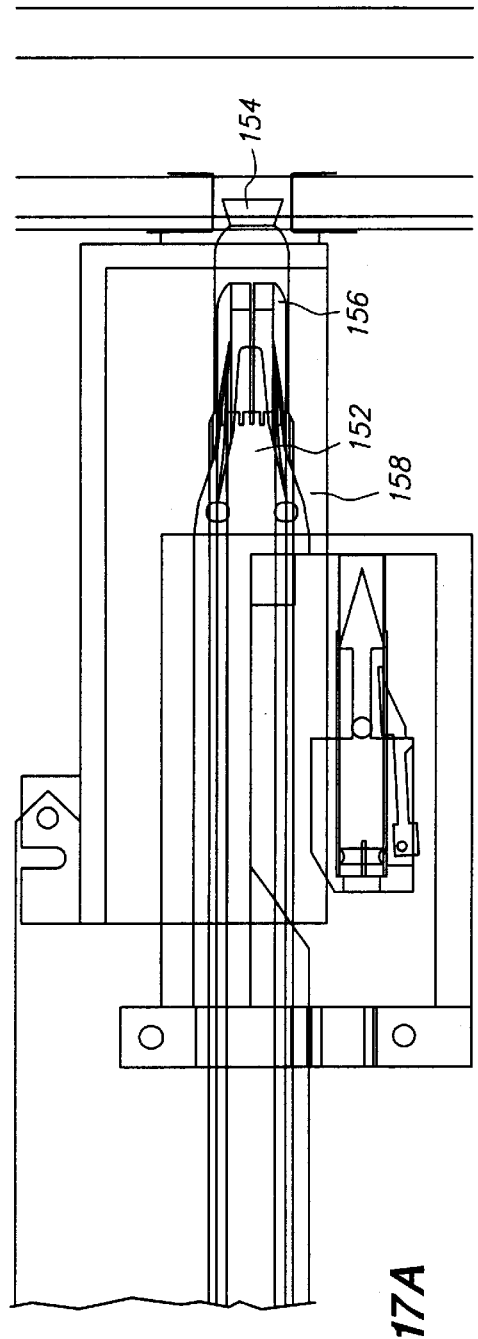
FIG. 17A is an enlarged view thereof.

Final rotation of the knob 160 brings about the withdrawal of the holder tube 154 and the expander tube 156 from the puncture site, which thereby aids in removal of the deployment system 150 from the vessel, as illustrated in FIGS. 17–17A.

The trocars and anastomosis devices described above can be single piece or multi-piece devices which are formed by laser cutting or punching from a tube or sheet of material. The devices may be provided in varying sizes to join vessels of different sizes.

Although the invention has been principally discussed with respect to coronary bypass surgery, the trocar and/or anastomosis devices of the present invention may be used in other types of anastomosis procedures. For example, the trocar and/or anastomosis device may be used in femoral-femoral bypass, vascular shunts, subclavian-carotid bypass, organ transplants, and the like.

The trocar and/or anastomosis devices may be made of any known material which can be elastically or plastically deformed such as stainless steel, nickel titanium alloys, polymer materials, and the like.

While the invention has been described in detail with reference to the preferred embodiments thereof, it will be apparent to one skilled in the art that various changes and modifications can be made and equivalents employed, without departing from the present invention.

What is claimed is:

1. A deployment system for forming an incision in a wall of a target vessel and delivering an anastomosis device for connecting an end of a graft vessel to a target vessel at the site of the incision, the deployment system comprising:
   a holder tube;
   a deployment tube for cooperating with the holder tube; and
   a rotatable control, whereby rotation of the control causes relative slidable movement between the holder tube and and the deployment tube.

2. The deployment system of claim 1, further comprising a trocar, the holder tube being slidably disposed within the trocar.

3. The deployment system of claim 2, wherein the trocar comprises a tubular member having a passage therein through which the anastomosis device is deliverable to the incision site.

4. The deployment system of claim 2, further comprising a tissue punch having a piercing element at a distal end thereof for forming a puncture, wherein the piercing element comprises a cutting blade which is movable with respect to the trocar such that the cutting blade can be moved from a cutting position at which the cutting blade is exposed to a retracted position at which the cutting blade is not exposed.

5. The deployment system of claim 4, wherein the piercing element includes a vessel wall piercing portion and a trimming portion, the piercing portion forming the incision upon insertion of the distal end of the member into the vessel wall and the trimming portion removing tissue around the incision upon retraction of the member.

6. An anastomosis device deployment system comprising:
   a tool having a rotatable control member;
   a holder tube attached to the tool, the holder tube having a distal end configured to hold the anastomosis device with an attached graft vessel; and
   an deployment member positioned within the holder and slidable with respect to the holder to a position at which the deployment member is positioned within the anastomosis device and thereby deploys the anastomosis device.

7. The system of claim 6, further comprising a trocar movable with respect to the holder tube to form an opening in a target vessel to receive the anastomosis device and attached graft vessel.

8. The system of claim 7, wherein the tool includes three cam grooves, and the trocar, holder tube and deployment member each have a follower member engaged in one of the cam grooves to move the trocar, holder tube and deployment member with respect to one another upon rotation of the control member.

9. The system of claim 8, wherein the tool includes at least one rotatable cylinder, said cam grooves being disposed on the at least one cylinder.

10. The system of claim 6, further comprising a tissue punch having a piercing element for establishing an initial puncture of a vessel wall.

11. The system of claim 6, further comprising a compliant mechanical stop.

12. A method of performing anastomosis comprising:
   providing a deployment tool having a trocar, an expander, a holder tube holding a one-piece tubular anastomosis device having an end of a graft vessel everted around the anastomosis device, and a rotatable control knob for moving the trocar, the expander tube and the holder tube relative to one another;
   rotating the control knob to puncture a target vessel with the trocar;
   rotating the control knob to insert the tubular anastomosis device with everted graft vessel into the puncture in the target vessel;
   rotating the control knob to radial expanding the tubular anastomosis device with the expander to cause a portion of the anastomosis device to fold outward forming a first annular flange; and
   rotating the control knob to form a second annular flange on the anastomosis device to trap a wall of the target vessel between the first and second annular flanges and seal the graft vessel to the target vessel.

13. The method of claim 12, wherein enlargement of an internal diameter of the anastomosis device with the expander tube causes the formation of the first flange.

14. The method of claim 12, wherein the anastomosis device is expanded by advancing the expander with an outer diameter greater than an inner diameter of the anastomosis device into the anastomosis device.

15. The method of claim 12, wherein the device is expanded by the expander in the form of an inflatable balloon.

16. The method of claim 12, wherein the radial expansion of the anastomosis device causes a portion of the device to bend at a plurality of hinges to form the first annular flange.

17. The method of claim 12, wherein the first and second annular flanges each form an angle between about 45 and 100 degrees with an axis of the device.

18. The method of claim 12, wherein the deployment tool further comprises a tissue punch, wherein rotation of the control knob causes advancement of the tissue punch into the target vessel prior to puncturing thereof by the trocar.

* * * * *